United States Patent
Wang et al.

(10) Patent No.: US 11,453,860 B2
(45) Date of Patent: Sep. 27, 2022

(54) GPC3 AND ASGPR1 DOUBLE-TARGETED TRANSGENIC IMMUNE EFFECTOR CELL AND USE THEREOF

(71) Applicant: CRAGE MEDICAL CO., LIMITED, Kowloon (HK)

(72) Inventors: Huamao Wang, Shanghai (CN); Xiumei Cai, Shanghai (CN); Hongxia Zhao, Shanghai (CN); Bo Song, Shanghai (CN); Yuanmei Chen, Shanghai (CN); Yinyu Zhu, Shanghai (CN)

(73) Assignee: CRAGE MEDICAL CO., LIMITED, Mongkok Kowloon (HK)

( * ) Notice: Subject to any disclaimer, the term of this patent is extended or adjusted under 35 U.S.C. 154(b) by 0 days.

(21) Appl. No.: 15/532,965

(22) PCT Filed: Nov. 30, 2015

(86) PCT No.: PCT/CN2015/095938
§ 371 (c)(1),
(2) Date: Jun. 2, 2017

(87) PCT Pub. No.: WO2016/086813
PCT Pub. Date: Jun. 9, 2016

(65) Prior Publication Data
US 2018/0201902 A1    Jul. 19, 2018

(30) Foreign Application Priority Data
Dec. 4, 2014   (CN) .......................... 201410736009.9

(51) Int. Cl.
| | |
|---|---|
| C12N 5/0783 | (2010.01) |
| C12N 5/10 | (2006.01) |
| A61K 39/395 | (2006.01) |
| C12N 15/63 | (2006.01) |
| C07K 14/00 | (2006.01) |
| C07K 16/28 | (2006.01) |
| A61K 35/17 | (2015.01) |
| A61P 35/00 | (2006.01) |
| C07K 14/725 | (2006.01) |
| C07K 14/705 | (2006.01) |
| C07K 16/30 | (2006.01) |
| C12N 15/86 | (2006.01) |
| A61K 39/00 | (2006.01) |

(52) U.S. Cl.
CPC ............ *C12N 5/0636* (2013.01); *A61K 35/17* (2013.01); *A61K 39/395* (2013.01); *A61P 35/00* (2018.01); *C07K 14/00* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 16/2851* (2013.01); *C07K 16/303* (2013.01); *C12N 5/10* (2013.01); *C12N 15/63* (2013.01); *C12N 15/86* (2013.01); *A61K 2039/505* (2013.01); *C07K 2317/622* (2013.01); *C07K 2319/02* (2013.01); *C07K 2319/03* (2013.01); *C07K 2319/33* (2013.01); *C12N 2740/15043* (2013.01)

(58) Field of Classification Search
CPC ............ C12N 5/0636; C07K 14/70521; C07K 16/303
See application file for complete search history.

(56) References Cited

U.S. PATENT DOCUMENTS

| | | | |
|---|---|---|---|
| 8,632,982 B2 | 1/2014 | Hu et al. | |
| 2013/0004427 A1* | 1/2013 | El-Sayed | A61K 47/48176 424/9.3 |
| 2013/0280220 A1 | 10/2013 | Ahmed et al. | |
| 2016/0215261 A1 | 7/2016 | Li et al. | |

FOREIGN PATENT DOCUMENTS

| | | |
|---|---|---|
| CN | 102803955 A | 11/2012 |
| CN | 103833852 A | 6/2014 |
| CN | 104140974 A | 11/2014 |
| EP | 2995682 A1 | 3/2016 |
| WO | 2013/126726 A1 | 8/2013 |
| WO | 2014/180306 A1 | 11/2014 |

OTHER PUBLICATIONS

Gao et al. "Development of T Cells Redirected to Glypican-3 for the Treatment of Hepatocellular Carcinoma" Clin Cancer Res Published Online Oct. 15, 2014, pp. OF1 to OF11 (Year: 2014).*
Cao et al. "Characterization of a single-chain variable fragment (scFv) antibody directed against the human asialoglycoprotein receptor" Biotechnol. Appl. Biochem. (2006) 44, 65-72 (Year: 2006).*
Wilkie et al. "Dual Targeting of ErbB2 and MUC1 in Breast Cancer Using Chimeric Antigen Receptors Engineered to Provide Complementary Signaling", J Clin Immunol (2012) 32:1059-1070. (Year: 2012).*
Brayman et al. "MUC1: A multifunctional cell surface component of reproductive tissue epithelia" Reproductive Biology and Endocrinology 2004, 2:4.*
Shi et al. "Expression of Asialoglycoprotein Receptor 1 in Human Hepatocellular Carcinoma", Journal of Histochemistry & Cytochemistry 61(12) 901-909.*
Kloss et al., Combinatorial antigen recognition with balanced signaling promotes selective tumor eradication by engineered T cells, Nat Biotechnol. Jan. 2013 ; 31(1): 71-75 (Year: 2013).*

(Continued)

*Primary Examiner* — Blaine Lankford
(74) *Attorney, Agent, or Firm* — Kilpatrick Townsend & Stockton LLP

(57) ABSTRACT

Provided are a GPC3 and ASGPR1 double-targeted transgenic immune effector cell and use thereof. The cell is an immune effector cell capable of identifying the gene modification of GPC3 and ASGPR1 simultaneously, and the cell can be used in the treatment of GPC3 and ASGPR1 double positive tumours, such as liver cancer.

11 Claims, 3 Drawing Sheets

Specification includes a Sequence Listing.

(56) References Cited

OTHER PUBLICATIONS

Wang, Wei et al; Recent Develop. of Liver Targeted Drug Delivery Sys. Based on Nanotechnology; Polymer Bulletin; Jan. 31, 2013, No. 1, 137-154.
Extended European Search Report in EP Application 15865161.2 dated Jun. 11, 2018; 12 pages.
Chen, C. et al.; "Development of T cells carrying two complementary chimeric antigen receptors against glypican-3 and asialoglycoprotein receptor 1 for the treatment of hepatocellular carcinoma"; Cancer Immunology Immunotherapy; Springer, Berlin/Heidelberg; vol. 66, No. 4; Dec. 29, 2016; pp. 475-489.
Duong, C.PM. et al.; "Enhancing the specificity of T-cell cultures for adoptive immunotherapy of cancer"; Immunotherapy; Future Medicine; London; vol. 3, No. 1; Jan. 1, 2011; pp. 33-48.
Hombach, A.A. et al.; "Costimulation by chimeric antigen receptors revisited the T cell antitumor response benefits from combined CD28-0X40 signalling"; International Journal of Cancer; vol. 129, No. 12; Mar. 29, 2011; pp. 2935-2944.
Hubbard, A.L. et al.; "An Electron Microscope Autoradiographic Study of the Carbohydrate Recognition Systems in Rat Liver"; J.Cell Biology; vol. 83; Oct. 1979; pp. 65-81.
Li, J. et al.; "Detection of Cirulcating Tumor Cells in Hepatocellular Carcinoma Using Antibodies against Asialoglycoprotein Receptor, Carbamoyl Phosphate Synthetase 1 and Pan-Cytokeratin"; PLOS One; vol. 9, No. 4; Apr. 2014; 9 pages.
Morell, A.G. et al.; "The Role of Sialic Acid in Determining the Survival of Glycoproteins in the Circulation"; The Journal of Biological Chemistry; vol. 246, No. 5; Mar. 10, 1971; pp. 1461-1467.
Mu, Hong, et al.; "Identification of biomarkers for hepatocellular carcinoma by semiquantitative immunocytochemistry"; World Journal of Gastroenterology; vol. 20, No. 19; Jan. 1, 2014; pp. 5826-5838.
Poelstra, K. et al.; "Drug targeting to the diseased liver"; Journal of Controlled Release; vol. 161; 2012; pp. 188-197.
Sadelain M. et al.; "The Basic Principles of Chimeric Antigen Receptor Design"; Cancer Discovery; vol. 3, No. 4; Apr. 1, 2013; pp. 388-398.
Schwartz, A.L. et al.; "Difficulties in the Quantification of Asialoglycoprotein Receptors on the Rat Hepatocyte"; The Journal of Biological Chemistry; vol. 255, No. 19; Oct. 10, 1980; pp. 9033-9036.
Schwartz, A.L. et al.; "Kinetics of Internalization and Recycling of the Saisloglycoprotein Receptor in a Hepatoma Cell Line"; The Journal of Biological Chemistry; vol. 257, No. 8; Apr. 25, 1982; pp. 4230-4237.
Weigel, P.H. et al.; "The Surface Content of Asialoglycoprotein Receptors on Isolated Hepatocytes Is Reversibly Modulated by Changes in Temperature"; The Journal of Biological Chemistry; vol. 258, No. 8; Apr. 25, 1983; pp. 5089-5094.
Zeitlin P.L. et al.; "Cell Surface Distribution and Intracellular Fate of Asialoglycoproteins: A Morphological and Biochemical Study of Isolated Rat Hepatocytes and Monolayer Cultures"; The Journal of Cell Biology; vol. 92; Mar. 1982; pp. 634-647.
Wilkie, S. et al.; "Retargeting of Human T Cells to Tumor-Associated MUC1: The Evolution of a Chimeric Antigen Receptor"; The Journal of Immunology; vol. 180; 2008; pp. 4901-4909.
Maher, J. et al.; "Targeting of Tumor-Associated Glycoforms of MUC1 with CAR T Cells"; Immunity Letters; vol. 45; Nov. 15, 2016; pp. 945-946.

\* cited by examiner

GPC3 AND ASGPR1 DOUBLE-TARGETED TRANSGENIC IMMUNE EFFECTOR CELL AND USE THEREOF

CROSS-REFERENCE TO RELATED APPLICATIONS

The present application is a § 371 National Phase Application of PCT/CN2015/095938, filed Nov. 30, 2015, which application claims priority to CN 201410736009.9, filed Dec. 4, 2014, the disclosures of which are hereby incorporated by reference in their entireties for all purposes.

Reference To Submission Of A Sequence Listing As A Text File

The Sequence Listing written in file SUBSEQ_096410-003000US-1051998_ST25.txt created on Dec. 21, 2017, 35,432 bytes, machine format IBM-PC, MS-Windows operating system, is hereby incorporated by reference in its entirety for all purposes.

TECHNICAL FIELD

The present invention relates to the field of immunotherapy of cancer, and more particularly, the present invention relates to a transgenic immune effector cell dual-targeting GPC3 and ASGPR1 and uses thereof.

BACKGROUND

The role of T lymphocytes in tumor immune response attracts more and more attention. T lymphocytes-based adoptive immunotherapy acquires a certain effect in some tumors, and such immunotherapeutic approaches can overcome disadvantages of antibody treatment, however, the effect is still unsatisfactory in the majority of tumors. In recent years, according to the discovery that the recognition of target cells by CTL is specifically dependent on T lymphocyted receptor (T Cell Receptor, TCR), scFv of an antibody against tumor cells-associated antigens is fused to an intracellular signaling activation motif of T lymphocyte receeptor, such as CD3ζ or FcεRIγ to form a chimeric receptor antigen (chimeric antigen receptor, CAR), which can be genetically modified on the surface of T lymphocytes by way of lentivirus infection and the like. Such CAR T lymphocytes can selectively directing T lymphocytes to tumor cells in a non-limiting manner as major histocompatibility complex (MHC) and specifically kill the tumor. CAR T lymphocytes is a new immunotherapeutic strategy in the field of cancer immunotherapy.

Chimeric antigen receptor (CAR) comprises an extracellular binding domain, a transmembrane region and intracellular signaling region. Generally, the extracellular domain comprises scFv capable of recognizing a tumor-associated antigen, in transmembrane region, the transmembrane region of a molecule, such as CD8, CD28, is used, and in the intracellular signaling region, the intracellular signaling region of immunoreceptor tyrosine activation motif (ITAM) CD3ζ or FcεRIγ and a co-stimulatory signaling molecule, such as CD28, CD137, CD134 are adopted.

In the first generation of CAR T lymphocytes, the intracellular signaling region only comprises ITAM, wherein portions of a chimeric antigen receptor are connected in a form as follows: scFv-TM-ITAM. This type of CAR T can stimulate cytotoxic effects against a tumor, but secretion of cytokine is relatively small, and a lasting anti-tumor effect cannot be excited in vivo [Zhang T. et al. Chimeric NKG2D-modified T cells inhibit systemic T-cell lymphoma growth in a manner involving multiple cytokines and cytotoxic pathways, Can Res 2007, 67(22):11029-11036.].

In the second generation of CAR T lymphocytes subsequently developed, the intracellular signaling region of CD28 or CD137 (also named as 4-1BB) is added, wherein portions of the chimeric antigen receptor are connected in a form as follows: scFv-TM-CD28-ITAM or scFv-TM-CD137-ITAM. B7/CD28 or 4-1BBL/CD137 co-stimulatory effects occurred in intracellular signaling region lead to continued proliferation of T-lymphocytes, and the secretion level of cytokines, such as IL-2 and IFN-γ by T-lymphocyte is improved, while in vivo survival period and anti-tumor effects of CAR T are increased [Dotti G et al. CD28 costimulation improves expansion and persistence of chimeric antigen receptor modified T cells in lymphoma patients. J Clin Invest, 2011, 121(5): 1822-1826.].

In the third generation of CAR T lymphocytes developed in recent years, portions of the chimeric antigen receptor are connected in a form as follows: scFv-TM-CD28-CD137-ITAM or scFv-TM-CD28-CD134-ITAM, and in vivo survival period and anti-tumor effects of CAR T are further increased [Carpenito C., et al. Control of large established tumor xenografts with genetically retargeted human T cells containing CD28 and CD137 domains. PNAS, 2009, 106(9): 3360-3365.].

Although there are attractive prospects for CAR T lymphocytes in tumor immunotherapy, some potential risks need to be considered. For example, some normal tissues express a specific antigen with low expression which can be recognized by CAR, which can result in damage to normal tissue expressing the corresponding antigen by CAR T lymphocytes. For example, adoptive therapy of CAR T lymphocytes against carbonic anhydrase IX (CAIX) antigen expressed on tumor cells in renal cell carcinoma patients is the first clinical case, and also is the first reported case including off-target effects of CAR cells. After being infused with CAR T lymphocytes for several times, patients experienced 2-4 grade of liver toxicity. Reasons were analyzed as the low expression of CAIX in bile duct epithelial cells, the clinical trial was forced to be interrupted while any evaluation on therapeutic effects to patients was excluded [Stoter G. et al. Treatment of metastatic renal cell carcinoma with autologous T-lymphocytes genetically retargeted against carbonic anhydrase IX: first clinical experience. J clin oncol, 2006, 24(13): e20-e22; Ngo M C., et al. Ex vivo gene transfer for improved adoptive immunotherapy of cancer. Human Molecular Genetics, 2011, R1-R7]. Moreover, the threshold required to activate effector cells will be reduced by excessive co-stimulatory signals in CAR, such that the genetically modified T lymphocytes may also be activated in conditions of low level of antigen or in the absence of antigen, thereby resulting in the release of a large amount of cytokines which may lead to the so-called "cytokine storm". Such signal leakage will cause off-target cytotoxicity, thereby producing non-specific tissue damage. For example, in the process of clinically treating a patient with advanced liver and lung metastases of colon cancer by using the third-generation of CAR against Her2, sudden death of the patient was caused by so-called "cytokine storm" due to low expression of Her2 in normal lung tissue [Morgan R A., et al. Report of a serious adverse event following the administration of T cells transduced with a chimeric antigen receptor recognizing Erbb2. Molecular Therapy, 2010, 18 (4): 843-851]. Therefore, there is an urgent need for resolving problems, such as low therapeutic efficacy and potential risks of CAR T cells, and develop a more effective method of killing tumor cells.

Phosphatidylinositol-proteoglycan-3 (Glypican-3, GPC3, also known as DGSX, GTR2-2, MXR7, OCI-5, SDYS, SGB, SGBS or SGBS1) is a cell surface protein belonging to heparan sulfate proteoglycans family. GPC3 gene encodes a core protein precursor of approximately 70-kDa, and the precursor protein is cleaved by furin into an amino terminus (N-terminal) peptide of approximately 40-kDa which is soluble and can enter blood and a carboxy terminus (C-terminal) peptide of approximately 30-kDa which is membrane-bound and contains 2 heparan sulfate (HS) sugar chains. GPC3 protein is attached to the cell membrane through glycosyl phosphatidylinositol (GPI).

GPC3 is highly expressed in fetal liver, while not expressed in normal adult liver tissue. GPC3 is expressed in hepatocellular carcinoma, and there is a very close relationship to the occurrence and development of liver cancer. It is not only of a higher detection rate at early stage of liver cancer, and with the development of liver cancer, the detection rate is further increased. The expression of GPC3 is not detected in the liver adenocarcinoma, cholangiocarcinoma, liver metastases, and 12 types of common solid tumors as well as 21 types of non-liver cancer cell lines. Moreover, GPC3 is also expressed in tumors, such as melanoma, ovarian clear cell carcinoma, yolk sac tumor, neuroblastoma.

Detecting liver cancer using anti-GPC3 antibody or studies on the use of antibody dependent (ADCC) or complement dependent (CDC) cell toxicity of anti-GPC3 antibody have been reported. Usually, a therapeutic antibody recognizes C-terminus of GPC3 protein. However, antibody treatment is limited by in vivo half-life of an antibody in blood circulation, and generally, the half-life is less than 23 days. Therefore, continuous administration and/or increase of the dose is required for the antibody therapy against tumors, which causes an increase in the cost of treatment for patients, and in some cases, the treatment even has to be terminated. Moreover, a therapeutic antibody, as a heterologous protein, is also possible to produce allergic reactions and there is also a risk of producing neutralizing antibodies in vivo against the therapeutic antibody.

Previous studies from the present inventors have shown that CAR T cells against GPC3 exhibits a very good killing effects on GPC3-positive liver cancer cells (CN 201310164725.x). However, although not expressed in most normal organs such as liver, but GPC3 is expressed in gastric glands (3/7 [43%]), tubular ((9/17 [53%]) and testicular germ cells. It should be considered that CAR T cells merely targeting GPC3 is likely to cause damage to these normal tissues (gastric glands, renal tubules and testicular germ cell).

Asialoglycoprotein receptor (ASGPR1, or named as ASGR1), also known as galactose receptor, is a transmembrane protein, the relative molecular mass of which is about 41,000, and which is consists of H1 and H2 subunits with different structures, wherein H1 is a major component of the receptor. Extracellular domain of ASGPR1 contains carbohydrate recognition domain (CRD), which can recognize and bind galactose residues and N-acetylgalactosamine residues. When CRD binds to a specific sugar residue, receptor-mediated endocytosis occurs. The main function of ASGPR1 is to remove apoptosis cells, lipoproteins and glycoproteins losing terminal sialic acid and exposing galactose residues or acetylgalactosamine residue in peripheral blood circulation, and also to mediate hepadnavirus (e.g., hepatitis B virus and hepatitis C virus) bind to and be taken into liver cells. ASGPR1 is predominantly expressed on the surface of liver parenchymal cells in liver sinusoidal of a mammalian, and of high density. On the surface of each cell, there can be up to 500,000 receptors. When there is a liver disease, such as hepatocellular carcinoma, hepatitis, cirrhosis, the expressed amount and function of ASGPR1 are reduced to some extent.

In the prior art, ASGPR1 as a target for the treatment of immune cells there is not report, much less the combination of GPC3, ASGPR1 with CAR immune effector cells.

SUMMARY OF THE INVENTION

The purpose of the present invention is to provide a GPC3 and ASGPR1 double-targeted transgenic immune effector cell and uses thereof.

In the first aspect of the present invention, a double-targeted chimeric antigen receptor (CAR) immune effector cell is provided, and the cell expresses the following chimeric receptor: a chimeric antigen receptor specifically recognizing GPC3; and a chimeric antigen receptor specifically recognizing ASGPR1.

In a preferred embodiment, the chimeric antigen receptor specifically recognizing GPC3 comprises: anti-GPC3 single chain antibody (scFv), T cell stimulatory signaling molecules.

In another preferred embodiment, the T cell stimulatory signaling molecules is selected from: CD3ζ or FcεRIγ; more preferably, the chimeric antigen receptor specifically recognizing GPC3 comprises (preferably 5'→3'): anti-GPC3 single chain antibody (scfv), transmembrane region of CD8, CD3ζ.

In another preferred embodiment, at 5' end of the anti-GPC3 single chain antibody (scFv), a reporter gene 1 (e.g., eGFP), F2A are further included, wherein reporter gene 1 is connected to the anti-GPC3 single chain antibody through F2A and the expression of the chimeric antigen receptor specifically recognizing GPC3 in a cell is present by reporter gene 1.

In another preferred embodiment, the chimeric antigen receptor specifically recognizing GPC3 possesses an amino acid sequence shown in SEQ ID NO: 17.

In another preferred embodiment, the chimeric antigen receptor specifically recognizing GPC3 is expressed by viral vectors; preferably a lentiviral vector, such as pWPT.

In another preferred embodiment, the chimeric antigen receptor specifically recognizing ASGPR1 comprises: anti-ASGPR1 single chain antibody (scFv), T cell activated co-stimulatory signaling molecule.

In another preferred embodiment, the T cell activated co-stimulatory signaling molecule is selected from: intracellular signal region of CD27, CD28, CD137, CD134, ICOS protein, or combinations thereof; more preferably, the chimeric antigen receptor specifically recognizing ASGPR1 comprises (preferably 5'→3'): anti ASGPR1 single chain antibody (scFv), transmembrane region of CD28 (CD28a), intracellular signaling region of CD28 (CD28b) and intracellular signaling region of CD137.

In another preferred embodiment, at 5' end of the anti ASGPR1 single chain antibody (scFv), a reporter gene 2 (e.g., mCherry), F2A are further included, wherein reporter gene 2 is connected to the anti ASGPR1 single chain antibody through F2A and the expression of the chimeric antigen receptor specifically recognizing ASGPR1 in a cell is present by reporter gene 2.

In another preferred embodiment, the chimeric antigen receptor specifically recognizing ASGPR1 possesses an amino acid sequence shown in SEQ ID NO: 24.

In another preferred embodiment, the chimeric antigen receptor specifically recognizing ASGPR1 is expressed by viral vectors; preferably a lentiviral vector, such as pWPT.

In another preferred embodiment, the immune effector cell is selected from: a T-lymphocyte, a NK cell or a NKT cell.

In another aspect of the present invention, use of the chimeric antigen receptor immune effector cell is provided, for preparing a kit for treating a tumor; wherein the tumor is a GPC3 and ASGPR1-double positive tumor; and preferably the tumor is liver cancer.

In another aspect of the present invention, a kit for treating a tumor is provided, comprising: the chimeric antigen receptor immune effector cell; and the tumor is a GPC3 and ASGPR1-double positive tumor; and preferably the tumor is liver cancer.

In another aspect of the present invention, a kit for preparing said chimeric antigen receptor immune effector cell is provided, comprising:

(a) expression construct a, comprising an expression cassette of the chimeric antigen receptor specifically recognizing GPC3 (which can be expressed in an immune cell); and (b) expression construct b, comprising an expression cassette of the chimeric antigen receptor specifically recognizing ASGPR1 (which can be expressed in an immune cell).

In a preferred embodiment, the expression cassette of the chimeric antigen receptor specifically recognizing GPC3 comprises a construct (expression vector) expressing the anti-GPC3 single chain antibody and T cell stimulatory signaling molecule; and preferably, it possesses a nucleotide sequence of SEQ ID NO: 17.

In a preferred embodiment, the expression cassette of the chimeric antigen receptor specifically recognizing ASGPR1 comprises a construct (expression vector) expressing the anti ASGPR1 single chain antibody and T cell activated stimulatory signaling molecule; and preferably, it possesses a nucleotide sequence of SEQ ID NO: 23.

In another preferred embodiment, the chimeric antigen receptor specifically recognizing GPC3 comprises: anti-GPC3 single chain antibody, T cell stimulatory signaling molecules; and preferably, the T cell stimulatory signaling molecules is selected from: CD3ζ or FcεRIγ;

the chimeric antigen receptor specifically recognizing ASGPR1 comprises: anti-ASGPR1 single chain antibody, T cell activated co-stimulatory signaling molecule; and preferably, the T cell activated co-stimulatory signaling molecule is selected from: intracellular signal region of CD27, CD28, CD137, CD134, ICOS protein, or combinations thereof.

Other aspects of the invention will be apparent to those skilled in the art from the disclosure herein.

MODES FOR CARRYING OUT THE INVENTION

Figure 1:
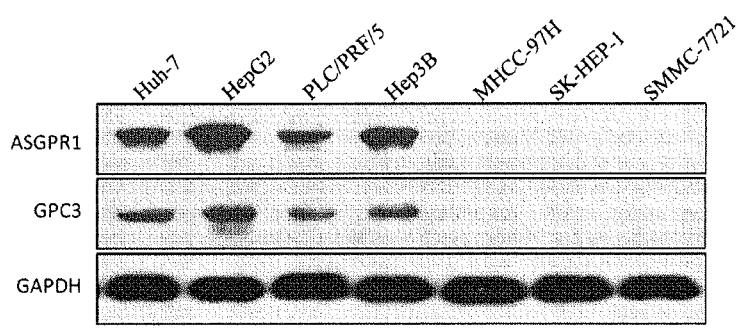
FIG. 1. Results of Western-blot for detecting expression level of ASGPR1 and GPC3 in various liver cancer cell lines.

The present inventors, through intensive study, for the first time discloses a genetically modified immune effector cell which can simultaneously recognize GPC3 and ASGPR1 and can be applied to treat GPC3 and ASGPR1 double-positive tumors (e.g., liver cancer).

The term "chimeric antigen receptor (CAR) immune effector cell" is well known in the art, and means an immune effector cell which expresses a tumor-specific chimeric antigen receptor using genetic modification techniques, exhibits some targeting, killing activity and persistence in vitro and in clinical trials, and is an adoptive cellular immunotherapy. The immune effector cells include, for example, T cells and NK cells.

Conventional methods for preparing "chimeric antigen receptor immune effector cells" are known to those skilled in the art and include expressing extracellular antigen (e.g., a tumor-associated antigen) binding region and intracellular domains of intracellular co-stimulatory cell molecules, such as one or more of CD28 (preferably CD28a, CD28b), CD137, CD27, CD3 ζ (preferably CD3 ζ intracellular domain), CD8, CD19, CD134, CD20, FcRγ. Upon binding to a corresponding ligand, the second signal of immune effector cells can be activated, the proliferation ability of immune cells and the secretion of cytokines can be enhanced, and the survival time of activated immune cells can be prolonged.

In the present invention, unless otherwise indicated, a tumor refers to a GPC3 and ASGPR1 double-positive tumor, and the tumor includes, for example, liver cancer.

In the study, the present inventors have unexpectedly discovered that phosphatidylinositol proteoglycan-3 (Glypican-3, GPC3, also known as DGSX, GTR2-2, MXR7, OCI-5, SDYS, SGB, SGBS or SGBS1) and asialoglycoprotein receptor (ASGPR1, also known as ASGR1) are co-expressed in liver cells, which has not been reported in the literature so far.

Based on this new discovery of co-expression of GPC3 and ASGPR1 and long-term experience in study, the present inventors designed a dual-targeting immune effector cell based on both of the proteins, which contains chimeric antigen receptor recognizing GPC3 (GCAR) and chimeric costimulatory receptor recognizing ASGPR1 (ACCR).

For the immune effector cell of the present invention, in one chimeric receptor, the extracellular domain contains a polypeptide recognizing GPC3, and the intracellular domain contains T cell stimulatory signal (e.g. ITAM motif of CD3ζ or FcεRIγ), named as GCAR; in another chimeric receptor, the extracellular domain contains a polypeptide recognizing ASGPR, and the intracellular domain contains T cell activated co-stimulatory signaling segment (which may be intracellular signaling segment of CD28, CD137, or other co-stimulatory signaling molecule), named as ACCR. Each of the chimeric receptor contains a transmembrane region. The polypeptide recognizing GPC3 or ASGPR can be a ligand protein, a small molecular polypeptide, a single chain antibody, a single domain antibody or other antibody fragment.

The nucleic acid sequence encoding chimeric receptor of the present invention may be in a form of DNA or RNA. The form of DNA includes cDNA, genomic DNA, or artificially synthesized DNA. DNA may be single-stranded or double-stranded. DNA may be a coding or non-coding strand. The nucleic acid codons of the present invention encoding the amino acid sequence of a chimeric antigen receptor protein may be degenerate, that is, various degenerate nucleic acid sequences encoding the same amino acid sequence are encompassed within the scope of the invention. Degenerate nucleic acid codons encoding corresponding amino acids are well known in the art. The present invention also relates to variants of the above polynucleotides, which encode polypeptides having the same amino acid sequence as the present invention or fragments, analogs and derivatives of the polypeptides. Such variants of polynucleotides may be naturally occurring allelic variants or non-naturally occurring variants. Such nucleotide variants include substitution variants, deletion variants, and insertion variants. As is known in the art, an allelic variant is an alternative form of a polynucleotide, which can be a substitution, deletion or insertion of one or more nucleotides while won't substantially change the function of the encoded polypeptide.

Monoclonal antibodies specifically recognizing C-terminal epitope of human GPC3 have been disclosed in, for example, CN 101186650A (Chugai Pharmaceutical Co Ltd.). In addition, according to a literature, Advances in Liver Cancer Antibody Therapies: A Focus on Glypican-3 and Mesothelin, BioDrugs 2011 Oct. 1; 25 (5): 275-284, other known monoclonal antibodies specifically recognizing C-terminal epitope, including GC33 and hGC33, are also reported, wherein the antigenic determinant of GPC3 is 524-563 amino acid residues at C-terminal. And other monoclonal antibodies, such as GPC3-C02 and 1G12, were also reported. These disclosed monoclonal antibodies can be used to prepare the single chain antibody portion of the chimeric antigen receptor encoded by the nucleic acid of the invention. Other monoclonal antibodies recognizing C-terminal epitope of GPC3 can be used in the present invention in a suitable manner. Monoclonal antibodies against heparan sulfate chains of GPC3 have also been reported (Gao W, Kim H, Feng M, Phung Y, Xavier C P, Rubin J S, Ho M. Inactivation of Wnt signaling by a human antibody that recognizes the heparan sulfate chains of glypican-3 for liver cancer therapy. Hepatology. 2014 August; 60(2):576-87).

As a preferred embodiment of the present invention, single chain antibody (scFv) specifically recognizing human GPC3 is used. Single-chain antibody can be prepared by genetic engineering methods or chemical synthesis methods according to the sequences of GPC3 monoclonal antibodies disclosed above. As used herein, the term "single chain antibody (scFv) fragment" refers to an antibody fragment which is a ecombinant protein comprising a heavy chain variable region (VH) linked to a light chain variable region (VL) by a linker, and the linker associates the two domains to form an antigen-binding site. Generally, scFv is ⅙ of a complete antibody in size. A single chain antibody is preferably one amino acid chain sequence encoded by one nucleotide chain. Single chain antibodies used in the present invention may be further modified by routine techniques known in the art, such as deletion, insertion, substitution, addition of amino acid, and/or recombination and/or other modification methods, and such techniques can be used alone or in combination. Methods for introducing such modification in the DNA sequences according to the amino acid sequence of an antibody are well known to those skilled in the art; see, for example Sambrook, "Molecular Cloning: A Laboratory Manual", Cold Spring Harbor Laboratory (1989) N.Y. The modification is preferably carried out at the nucleic acid level. The single-chain antibody said above may further include derivatives thereof. In the present invention, "derivatives" include, for example, derivatives of the antibody obtaining by phage display techniques. Efficiency of phage antibodies binding GPC3 antigen epitope can be increased by, for example, surface plasmon resonance technology used in BIAcore system (Schier, human antibody hybridomas 7 (1996), 97-105; Malmborg, Immunol. Methods., 183 (1995), 7-13). The method also includes, for example, the preparation method for chimeric antibodies disclosed in WO 89/09622, the preparation method for humanized antibodies disclosed in EP-A10239400 and WO90/07861, and the preparation method for xenogeneic antibodies disclosed in WO91/10741, WO94/02602 and WO96/33735, for example, preparing human antibodies in mice.

The term "specific recognition" used in the present invention means that the bispecific antibody of the invention does not or substantially does not cross-react with any polypeptide other than the target antigen. The degree of specificity can be determined by immunological techniques including, but not limited to, immunoblotting, immunoaffinity chromatography, flow cytometry, and the like. In the present invention, specific recognition is preferably determined by flow cytometry, and in particular, the criteria for specific recognition can be determined by a skilled person in light of the common knowledge in the art.

Transmembrane domain can be selected from the transmembrane domain of a protein such as CD8 or CD28. CD8 or CD28 is a natural marker on the surface of T cells. Human CD8 protein is a heterodimer consisting of $\alpha\beta$ or $\gamma\delta$ chains. In one embodiment of the present invention, transmembrane domain is selected from the transmembrane domain of CD8a or CD28. In addition, CD8a hinge region is a flexible region, so that the transmembrane domain and hinge region of CD8 or CD28 can be used to link the target recognition domain and intracellular signal domain of chimeric antigen receptor CAR or CCR.

Intracellular signal domain of GCAR can be selected from the intracellular signal domain of CD3 or FcεRIγ; and intracellular signal domain of ACCR can be selected from the intracellular signal domain of CD27, CD28, CD137, CD134, ICOS protein or combinations thereof. CD3 molecule consists of five subunits, in which CD3ζ subunit (also known as CD3 zeta, abbreviated as Z) contains three ITAM motifs, which is an important signal transduction region in TCR-CD3 complex. CD3δZ is a truncated CD3ζ sequence without ITAM motif, and is generally used to construct a negative control in the practice of the present invention. FcεRIγ is mainly distributed on the surface of mast cells and basophils, which contains an ITAM motif and is similar to CD3ζ in structure, distribution and function. In addition, as said above, CD27, CD28, CD137, CD134, ICOS are co-stimulatory signal molecules, and after binding to the respective ligands, co-stimulatory effect of the intracellular signal region of these molecules results in the continuous proliferation of T lymphocytes and increases the level of cytokines, such as IL-2 and IFN-γ secreted by T lymphocytes, while improving the survival and anti-tumor effect of T lymphocytes in vivo.

Anti-GPC3 chimeric receptor protein GCAR encoded by the nucleic acid of the present invention may be sequentially connected as follows: scFv(GPC3)-CD8-CD3ζ; wherein scFv(GPC3) represents a single chain antibody recognizing GPC3, and CD8 represents transmembrane region of CD8.

Anti-ASGPR1 chimeric receptor protein ACCR encoded by the nucleic acid of the present invention may be sequentially connected as follows: Fv(ASGPR)-CD28a-CD28b-CD137; wherein, in the chimeric antigen receptor protein, Fv(ASGPR1) represents single domain antibody recognizing ASGPR1; CD28a represents transmembrane region of CD28 molecules, CD28b represents intracellular signaling region of CD28 molecule, and CD137 represents intracellular signaling region of CD137 molecule.

The present invention further includes a nucleic acid construct or vector comprising the nucleic acid encoding a chimeric antigen receptor protein expressed on the surface of T lymphocytes. In a specific embodiment, the vector used in the present invention is a lentiviral plasmid vector pPWT-eGFP. The plasmid belongs to the third-generation of self-inactivating lentiviral vector system. The system consists of three plasmids, that is, packaging plasmid psPAX2 encoding Gag/Pol protein, Rev protein; envelope plasmid PMD2.G encoding VSV-G protein; and blank vector pPWT-eGFP, which can be used to introduce a nucleic acid sequence of interest through recombination, i.e. CAR-encoding nucleic acid sequence. In the blank vector pPT-eGFP (the vector itself is a mock in the subsequent experiments), the expression of enhanced green fluorescent protein (eGFP) was regulated by elongation factor-1α promoter (EF-1α). And in the recombinant expression vector pWPT-eGFP comprising a target nucleic acid sequence encoding CAR, the co-expression of eGFP and CAR is achieved by a ribosome jumping sequence 2A (abbreviated as F2A) from foot-and-mouth disease virus (FMDV).

The present invention further includes a virus comprising the above-described vector. The viruses of the present invention include infectious viruses after packaging and also include viruses to be packaged that contain components necessary for the package of infectious viruses. Other viruses which can transfect T lymphocytes and their corresponding plasmid vectors known in the art can also be used in the present invention.

In one embodiment of the invention, the virus is a lentivirus comprising the pWPT-eGFP-F2A-CAR recombinant vector described above (i.e. containing scFv (GPC3)-CAR).

The present invention further includes a genetically modified T lymphocyte, which is transduced with a nucleic acid of the present invention or transduced with the above-mentioned recombinant plasmid containing the nucleic acid of the present invention or a viral system containing the plasmid. Conventional nucleic acid transduction methods in the art, including non-viral and viral transduction methods, can be used in the present invention. Non-viral transduction methods include electroporation and transposon methods. Recently, nucleofector nuclear transfection instrument developed by Amaxa can directly introduce foreign genes into nucleus to achieve highly efficient transduction of target genes. In addition, compared with conventional electroporation, the transduction efficiency of transposon system based on Sleeping Beauty system or PiggyBac transposon was significantly improved. The combination of nucleofector transfection instrument and SB Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10.], and high transduction efficiency and site-directed integration of target genes can be achieved by this method. In one embodiment of the invention, the transduction method of a T lymphocyte modified by a chimeric antigen receptor gene is a transduction method based on a virus such as a retrovirus or a lentivirus. The method has the advantages of high transduction efficiency and stable expression of exogenous gene, and the time for in vitro culturing T lymphocytes to clinical level can be shorten. The transduced nucleic acid is expressed on the surface of the transgenic T lymphocytes by transcription, translation. In vitro cytotoxicity assay performed on various cultured tumor cells demonstrated that the T lymphocytes modified by anti-GPC3 chimeric antigen receptor gene of the present invention have highly specific tumor cell killing effects (also known as cytotoxicity). Therefore, the nucleic acid encoding a chimeric antigen receptor protein of the present invention, a plasmid comprising the nucleic acid, a virus comprising the plasmid, and a transgenic T lymphocyte transfected with the nucleic acid, plasmid or virus described above can be effectively used in tumor immunotherapy.

The present invention also relates to a kit comprising said dual-targeted immune effector cells. The present invention also relates to a kit for preparing the dual targeted immune effector cells of the present invention. After reading the contents of the present invention, those skilled in the art will understand how to prepare said kit. The kit may also contain instructions for using the kit.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer.

Example 1. Detection of Expression Level of ASGPR1 and GPC3 in Various Cell Lines of Liver Cancer and Establishment of Stable Expression Cell Lines of Liver Cancer 1. Detection of Expression Level of ASGPR1 and GPC3 in Various Liver Cancer Cell Lines Firstly the present inventors examined the expression of ASGPR1 and GPC3 in various liver cancer cell lines.

Western-blot detection method: liver cancer cells HepG2, Huh-7, Hep3B, PLC/PRF/5, MHCC-97H, SK-HEP-1 and SMMC-7721 in good growth were washed with D-PBS for two times respectively, and afterwards, T-REP tissue cell lysis liquid was added, placed on ice for 1 h, centrifuged at 12000 rpm for 10 mins for collecting the supernatant. BCA method was used for quantification according to the instruction of BCA assay kit. Absorbance at 570 nm wavelength was detected with UV spectrophotometer. Then the above collected samples were subject to 12% SDS-PAGE electrophoresis, wherein 20 μg of total protein was loaded respectively. After SDS-PAGE electrophoresis, 5% skim milk was used for blocking for 2 hours, and then mouse anti-human GPC3 monoclonal antibody (Shanghai Ruijin Biotechnology Co., Ltd.) and mouse anti-human ASGPR1 monoclonal antibody (Abcam Inc.) were added at 4° C. overnight. The next day, 0.5% PBST was used for washing for three times, and then HRP-goat anti-mouse antibody (Shanghai Ruijin Biotechnology Limited) was added, incubated at room temperature for 1 hour and washed with 0.5% PBST for three times. Substrate was added for reaction, exposed and developed.

Western-blot results are shown in FIG. 1. ASGPR1 and GPC3 proteins were expressed in different extent in cells except MHCC-97H, SK-HEP-1 and SMMC-7721 cells.

Flow cytometry: liver cancer cells HepG2, Huh7, Hep3B, PLC/PRF/5, MHCC-97H, SK-HEP-1 and SMMC-7721 in good growth were digested with 10 mM EDTA and dispersed in a flow tube. Cells were centrifuged at 3000~4000 rpm for 5 min, and washed with 2 mL 1% NCS PBS for two times. Mouse anti-human GPC3 monoclonal antibody (Shanghai Ruijin Biotechnology Co., Ltd.) and mouse anti-human ASGPR1 monoclonal antibody (Abcam company, final concentration of 5 μg/mL) were added, and placed into an ice bath for 45 min; and then washed with 2 mL 1% NCS PBS for 2 times. Goat anti-mouse IgG-FITC (Shanghai Rui Jin Biotechnology Co., Ltd.) was added, placed in an ice bath for 45 min, and washed with 1% NCS PBS for 2 times. Cells were re-suspended in 200~500 μL 1% NPBS, and detected on the machine.

Figure 2:
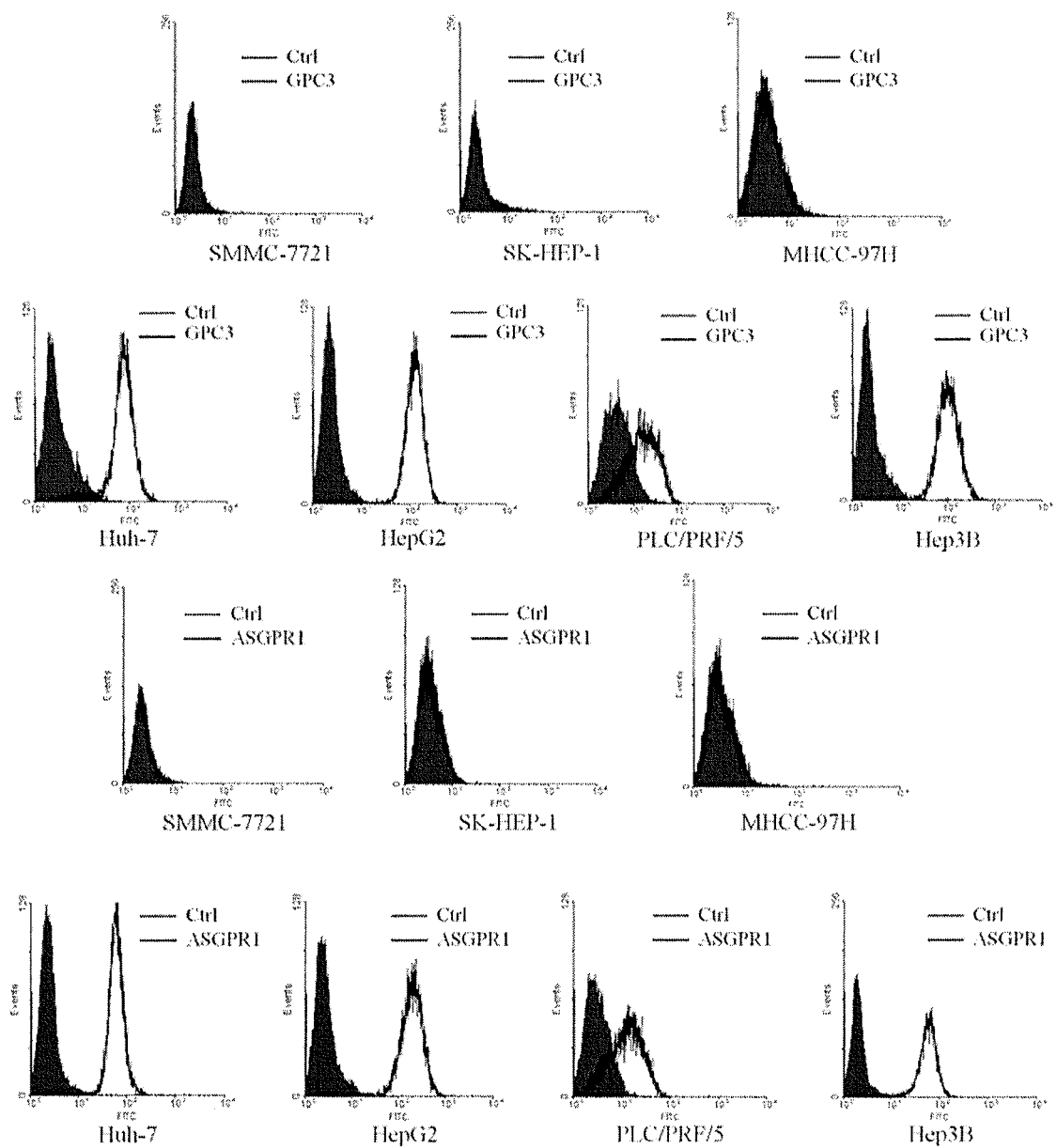
FIG. 2. Results of flow cytometry for detecting expression level of ASGPR1 and GPC3 in various liver cancer cell lines.

Result of flow cytometry is shown in FIG. 2. ASGPR1 and GPC3 were expressed in different extent in cells except MHCC-97H, SK-HEP-1 and SMMC-7721 cells, which were consistent with Western-blot.

2. Construction and Identification of Liver Cancer Cell Lines Stably Expressing ASGPR1 and GPC3

Liver cancer cells MHCC-97H were GPC3/ASGPR1 double-negative cells, and double-negative cell lines MHCC-97H were selected to construct GPC3+, ASGPR1+ and GPC3+/ASGPR1+ overexpressing cell lines. Constructed cell lines MHCC-97H-G, MHCC-97H-A, MHCC-97H-GA represent MHCC-97H cell line expressing GPC3, MHCC-97H cell line expressing ASGPR1, and MHCC-97H cell line simultaneously expressing GCC3 and ASGPR1, respectively.

Construction of pWPT-GPC3 plasmid: full-length ORF nucleic acid fragment of GPC3 was obtained through amplification with upstream primer 5'-agcttacgcgtcctagcgctaccgg tcgccaccatggccgggaccgtgcgcacc-3' (SEQ ID NO: 1) and downstream primer 5'-CGAGGTCGACC-TATCAGTGCACCAGGAAGAAGAAGCAC-3' (SEQ ID NO: 2) and cDNA of Hep 3B cell as a template. PCR amplification conditions were: pre-denaturation at 94° C. for 4 min; denaturation at 94° C. for 40 s; annealing at 56° C. for 40 s; extension at 68° C. for 50 s; 30 cycles; followed by a total extension at 68° C. for 10 min. Amplified products were confirmed by agarose gel electrophoresis, double-digested with MluI and SalI, and inserted into lentiviral vector pWPT-eGFP double-digested with same enzymes. Positive clones were selected and sequenced, so as to obtain expression plasmid pWPT-GPC3 comprising encoding sequence (SEQ ID NO: 3) for full-length GPC3 protein (SEQ ID NO: 4).

Construction of pWPT-ASGPR1 plasmid: full-length ORF nucleic acid fragment of ASGPR was obtained through amplification with upstream primer 5'-gcttacgcgtcctagcgc-taccggtcgccaccatgaccaaggagtatcaagacc-3' (SEQ ID NO: 5) and downstream primer 5'-CGAGGTCGACCTAT-TAAAGGAGAGGTGGCTCCTGGCT-3' (SEQ ID NO: 6) and a plasmid comprising full length ORF of human ASGPR1 as a template. PCR amplification conditions were: pre-denaturation at 94° C. for 4 min; denaturation at 94° C. for 40 s; annealing at 56° C. for 40 s; extension at 68° C. for 50 s; 30 cycles; followed by a total extension at 68° C. for 10 min. Amplified products were confirmed by agarose gel electrophoresis, double-digested with MluI and SalI, and inserted into lentiviral vector pWPT-eGFP double-digested with same enzymes. Positive clones were selected and sequenced, so as to obtain expression plasmid pWPT-ASGPR1 comprising encoding sequence (SEQ ID NO: 7) for full-length ASGPR protein (SEQ ID NO: 8).

Lentivirus Package of GPC3 and ASGPR1:

(1) 293T cells, which were cultured to 6th-10th generation, were inoculated into a 10 cm dish at a density of $6 \times 10^6$, and cultured at 37° C., 5% CO2 overnight for transfection. The medium was DMEM containing 10% fetal bovine serum (PAA).

(2) Preparation of A solution: 10 μg of target gene plasmid pWPT-eGFP (i.e., Mock), pWPT-GPC3 and pWPT-ASGPR1 as well as package plasmid pPAX2 (7.5 μg) and envelope plasmid pMD2.G (3 μg) were dissolved into 800 μl of serum-free DMEM medium, respectively, and gently mixed.

(3) Preparation of B solution: 60 μg PEI (1 μg/l) was dissolved in 800 μl serum-free DMEM medium, mixed gently, and incubated at room temperature for 5 min.

(4) A solution was added into B solution, gently mixed, and incubated at room temperature for 20 min. 1.6 ml of transfection complex was then added into a 10 cm dish dropwise.

(5) After 4-5 h, 2% FBS in DMEM was changed for the transfected 293 T cells.

(6) Incubation was performed at 37° C. for 72 h, and the virus supernatant was collected.

Virus infection: 1 mL of virus supernatant was taken, polybrene was added at a final concentration of 0.6 μg/mL. Cells were re-suspended at $5 \times 10^4$, centrifuged at 2200 rpm, RT for 30 min for suspension infection. After centrifugation, the cells were re-suspended and 1 mL of fresh medium was supplemented. Cells were plated in a 6-well plate. After substantial confluence, cells were collected. And the expression of exogenous protein in mixed clones was detected by Western-blot.

Figure 3:
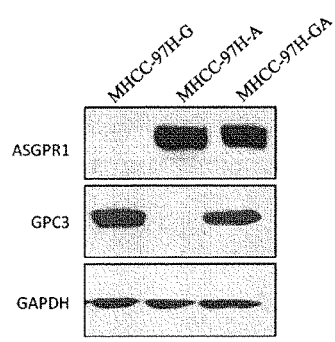
FIG. 3. Western-blot detection of expression of GPC3, ASGPR1 in MHCC-97H-G, MHCC-97H-A, MHCC-97H-GA stably transfected cell lines.

Results are shown in FIG. 3, wherein the expression of GPC3 and ASGPR1 and co-expression of GPC3 and ASGPR1 proteins were detected in MHCC-97H-G, MHCC-97H-A and MHCC-97H-GA three stably transfected cell lines respectively, which demonstrates that ASGPR1 and GPC3 stably transfected liver cancer cell lines were successfully constructed.

Example 2. Establishment of GCAR T Cell (or GZ T Cell), ACCR T Cell (or 28BB T Cell) And GZ+28BB T Cell 1. Construction of pWPT-eGFP-F2A-GPC3-CD3ζ scFv (GPC3) sequence was amplified by using single-stranded bifunctional antibody nucleotide GPC3 as template, the sequence of which can be found in Chinese Patent Application 201210480326.x as SEQ ID NO: 9. And the primer pair used in amplification are: upstream primer 5'-gatgttgtgatgactcagtctc-3' (SEQ ID NO: 9) and downstream primer 5'-gcgctggcgtcgtggttgaggagacggtgaccag-3' (SEQ ID NO: 10), used to amplify scFv (GPC3) (SEQ ID NO: 11, encoding SEQ ID NO: 12); and the target band is 746 bp in size. PCR amplification conditions were: pre-denaturation at 94° C. for 4 min; denaturation at 94° C. for 40 s; annealing at 58° C. for 40 s; extension at 68° C. for 40 s; 30 cycles; followed by a total extension at 68° C. for 10 min. PCR-amplified bands were confirmed by agarose gel electrophoresis to comply with the predicted fragment size.

Except for scFv(GPC3), nucleic acid sequences of other parts in GPC3 chimeric antigen receptor protein were obtained through PCR using SEQ ID NO: 1 disclosed in patent application NO. 201310108532.2 as template. In particular, CDg8-CD3ζ(Z) was amplified by using scFv (EFGR)-CD8-CD3ζ (SEQ ID NO: 1 in patent application 201310108532.2) as template and upstream primer 5'-accacgacgccagcgccgcgaccac-3' (SEQ ID NO:13) and downstream primer 5'-gaggtcgacctagcgaggggggcagggcctgcatgtgaag-3' (SEQ ID NO:14). PCR amplification conditions were: pre-denaturation at 94° C. for 4 min; denaturation at 94° C. for 40 s; annealing at 60° C. for 40 s; extension at 68° C. for 40 s; 25 cycles; followed by a total extension at 68° C. for 10 min. The target band is 549 bp in size. PCR-amplified bands were confirmed by agarose gel electrophoresis to comply with the predicted fragment size. eGFP nucleic acid fragments with F2A and CD8 signal peptide at 3' end was amplified from the lentiviral vector by using upstream primer 5'-cttacgcgtcctagcgctaccggtcgccacca tggtgagcaagggcgaggag-3' (SEQ ID NO: 15) and downstream primer 5'-cggcctggcggcgtggagcag-3' (SEQ ID NO: 16) and scFv(EGFR)-CD8-CD3ζ (SEQ ID NO: 1 in patent application 201310108532.2) disclosed in patent application 201310108532.2 as template. PCR amplification conditions were: pre-denaturation at 94° C. for 4 min; denaturation at 94° C. for 40 s; annealing at 56° C. for 40 s; extension at 68° C. for 50 s; 25 cycles; followed by a total extension at 68° C. for 10 min. PCR-amplified bands were confirmed by agarose gel electrophoresis to comply with the theoretical size, 883 bp.

The above amplified fragments of CD8-CD3ζ, eGFP nucleic acid fragment (mass of which was about 50 ng) with F2A and CD8 signal peptide at 3' end and equimolar of scFv(GPC3) fragment (mass of which was about 50 ng) were spliced and subjected to PCR. Splicing conditions were: pre-denaturation at 94° C. for 4 min; denaturation at 94° C. for 40 s; annealing at 60° C. for 40 s; extension at 68° C. for 140 s; 5 cycles; followed by a total extension at 68° C. for 10 min. After DNA polymerase and upstream primer 5'-cttacgcgtcctagcgctaccggtcgccaccatggtgagcaagggcgaggag-3' (SEQ ID NO: 15) as well as downstream primer 5'-gaggtcgacctagcgagggggcagggcctgcatg-3' (SEQ ID NO: 14) were supplemented, PCR was performed for 25 cycles. Amplification conditions were: pre-denaturation at 94° C. for 4 min; denaturation at 94° C. for 40 s; annealing at 60° C. for 40 s; extension at 68° C. for 140 s; 20 cycles; followed by a total extension at 68° C. for 10 min. A sequence comprising full length eGFP-F2A-GPC3-CD3 ORF (SEQ ID NO: 17, encoding SEQ ID NO: 18) was obtained through amplification, the theoretical size of which is 2161 bp. The amplified product was confirmed by agarose gel electrophoresis to comply with the theoretical size, and double-digested with MluI and SalI, and inserted into vector pWPT-eGFP digested with same enzymes. Positive clones were selected and sequenced, so as to obtain pWPT-eGFP-F2A-GPC3-CD3ζ.

2. Construction of pWPT-mCherry-F2A-ASGPR-CD28a-CD28b-CD137 Plasmid

The sequence of anti-ASGPR single domain antibody is shown in SEQ ID NO: 20, which was obtained by whole-gene sequence synthesis (SEQ ID NO: 19, encoding SEQ ID NO: 20). mCherry nucleic acid fragments with F2A and CD8 signal peptide at 3' end was obtained by whole-gene sequence synthesis. Except for anti-ASGPR single domain antibody, nucleic acid sequences of other parts in ASGPR-CD28a-CD28b-CD137 chimeric antigen receptor protein were obtained through PCR using SEQ ID NO: 3 disclosed in patent application NO. 201310108532.2 as template. In particular, scFv(EFGR)-CD8-28BBZ (SEQ ID NO: 3 in patent application 201310108532.2) was used as template, and upstream primer 5'-accacgacgccagcgccgcgaccac-3' (SEQ ID NO: 13) and downstream primer 5' GAGGTCGACCTACAGTTCACATCCTCCTTCT-3' (SEQ ID NO: 21) were used in amplification. PCR amplification conditions were: pre-denaturation at 94° C. for 4 min; denaturation at 94° C. for 40 s; annealing at 60° C. for 40 s; extension at 68° C. for 40 s; 25 cycles; followed by a total extension at 68° C. for 10 min. PCR-amplified bands were confirmed by agarose gel electrophoresis to comply with the theoretical size, 477 bp.

The above amplified fragments: mCherry nucleic acid fragment with F2A and CD8 signal peptide at 3' end, equimolar of anti-ASGPR single domain antibody and CD28a-CD28b-CD137 were spliced and subjected to PCR. Splicing conditions were: pre-denaturation at 94° C. for 4 min; denaturation at 94° C. for 40 s; annealing at 60° C. for 40 s; extension at 68° C. for 140 s; 5 cycles; followed by a total extension at 68° C. for 10 min. After DNA polymerase and upstream primer 5'-cttacgcgtcctagcgctaccggtcgccac-catggtgagcaagggcgaggag-3' (SEQ ID NO: 15) as well as downstream primer 5'-GAGGTCGACCTACAGTTCA-CATCCTCCT-3' (SEQ ID NO: 22) were supplemented, PCR was performed for 25 cycles. Amplification conditions were: pre-denaturation at 94° C. for 4 min; denaturation at 94° C. for 40 s; annealing at 60° C. for 40 s; extension at 68° C. for 140 s; 25 cycles; followed by a total extension at 68° C. for 10 min. A sequence comprising full length ORF of mCherry-F2A-ASGPR-CD28a-CD28b-CD137 (SEQ ID NO: 23, encoding SEQ ID NO: 24) was obtained through amplification, the theoretical size of which is 1711 bp. The amplified product was confirmed by agarose gel electrophoresis to comply with the theoretical size, and double-digested with MluI and SalI, and inserted into vector pWPT-eGFP digested with same enzymes. Positive clones were selected and sequenced, so as to obtain pWPT-mCherry-F2A-ASGPR-CD28a-CD28b-CD137.

Lentivirus Package of GCAR and ACCR:

(1) 293T cells, which were cultured to 6th-10th generation, were inoculated into a 10 cm dish at a density of 6×10⁶, and cultured at 37° C., 5% CO2 overnight for transfection. The medium was DMEM containing 10% fetal bovine serum (PAA).

(2) Preparation of A solution: 10 μg of target gene plasmid pWPT-eGFP (i.e., Mock), pWPT-eGFP-F2A-GPC3-CD3ζ and pWPT-mCherry-F2A-ASGPR-CD28a-CD28b-CD137 as well as package plasmid pPAX2 (7.5 μg) and envelope plasmid pMD2.G (3 μg) were dissolved into 800 μl of serum-free DMEM medium, respectively, and gently mixed.

(3) Preparation of B solution: 60 μg PEI (1 μg/μl) was dissolved in 800 μl serum-free DMEM medium, mixed gently, and incubated at room temperature for 5 min.

(4) A solution was added into B solution, gently mixed, and incubated at room temperature for 20 min. 1.6 ml of transfection complex was then added into a 10 cm dish dropwise.

(5) After 4-5 h, 2% FBS in DMEM was changed for the transfected 293 T cells.

(6) Incubation was performed at 37° C. for 72 h, and the virus supernatant was collected.

3. Infection of CTL Cells by Recombinant Lentivirus

Peripheral blood mononuclear cells (PBMC) were separated from blood of a healthy human donator by using Ficoll (from Biochrom) density gradient centrifugation according to standard procedure. Upon centrifugation, cells were washed with 1× phosphate buffer (PBS), and re-suspended into RPMI 1640 complete medium (Gibco). CTL were obtained from separated peripheral blood mononuclear cells through negative sorting method by using CTL beads (Stem Cell Technologies). Sorted CTL cells were tested for the purity of CTL cells through flow Cytometry, and if the positive rate of CTL cells is ≥95%, it is appropriate for the next operation. Quantum 007 lymphocyte culture medium (PAA) was added at a density of about $1\times10^6$/mL for culture, magnetic beads coated with anti-CD3 and CD28 antibodies (Invitrogen) were added at cell:magnetic bead of 1:1, and cells were stimulated and cultured for 24 h with recombinant human IL-2 at a final concentration of 100 U/mL. And then, CTL cells were infected by the above constructed recombinant lentivirus at MOI≈5. Infected cells were passaged every other day at a density of $5\times10^5$/mL and recombinant human IL-2 was supplemented in the lymphocyte culture medium at a final concentration of 100 U/mL.

4. Analysis of Positive Infection Rate of T Cells by Flow Cytometry

At the $8^{th}$ day of culture, infected CTL cells were detected by flow cytometry for the expression of different chimeric antigen receptors, detected eGFP or mCherry-positive cells were deemed as positive cells expressing chimeric antigen receptors due to the co-expression of eGFP and CAR as well as co-expression of mCherry and CCR. Positive ratio of CTL cells infected by the virus and expressing different chimeric antigen receptors are shown in table 1, with uninfected T lymphocytes as negative control. The positive rate demonstrates that certain positive rate of chimeric antigen receptor T cells recognizing GPC3 (GCAR T), chimeric co-stimulatory receptor T cells recognizing ASGPR1 (ACCR T cells) and GZ+28BB T cells can be obtained by lentivirus infection.

TABLE 1

| CTL cells transfected with following CARs | positive rate of infected CTL cells |
|---|---|
| Mock (control of blank vector) | 66% |
| GCAR T | 61% |
| ACCR T | 57% |
| GZ + 28BB T | 30% |

5. Detection of Expression of Target Gene in Infected T Cells by Western Blot

Infected Mock T cells, GCAR T cells, ACCR T cells, and GZ+28BB T cells were collected by centrifugation, cell lysis liquid was added, and proteins in cell were extracted and quantitatively determined by using BCA kit (Thermo). The above collected samples were subject to 12% SDS-PAGE electrophoresis, wherein 20 μg of total protein was loaded respectively. After SDS-PAGE electrophoresis, 5% skim milk was used for blocking for 2 hours, and then mouse anti-human CD3ζ monoclonal antibody (Sigma) and mouse anti-human CD28 antibody (Abcam) were added at 4° C. overnight. The next day, 0.5% PBST was used for washing, and then HRP-goat anti-mouse second antibody was added, incubated at room temperature for 1 hour and washed with 0.5% PBST. Substrate was added, exposed and developed.

Figures 4A, 4B:
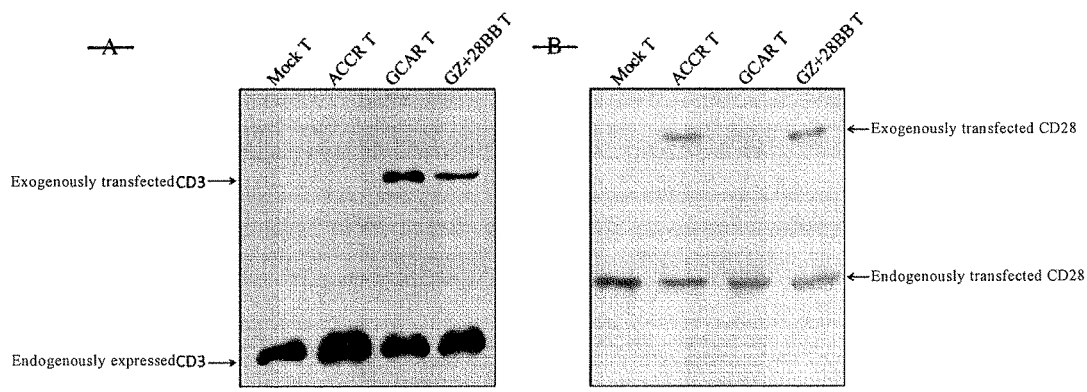
FIG. 4. Western-blot detection of expression of target genes in infected T cells.

Results are shown in FIGS. 4A-4B. FIG. 4A shows that only expression of endogenous CD3 was detected in Mock T and ACCR T cells, while expression of endogenous CD3 and expression of exogenously transfected CD3 were detected in GCAR T and GZ+28BB T cells. FIG. 4B shows that only the expression of endogenous CD28 was detected in Mock T and GCAR T cells, while the expression of endogenous CD28 and expression of exogenously transfected CD28 were detected in ACCR T and GZ+28BB T cells, which demonstrates that the cell lines stably transfected with chimeric antigen receptors were successfully constructed.

Example 3. In Vitro Cytotoxicity Experiment

Target cells: HepG2 cell (expressing endogenous GPC3 and ASGPR1, commercially available from ATCC), MHCC-97H and stably transfected liver cancer cell line MHCC-97H-G (highly expressing GPC3), MHCC-97H-A (highly expressing ASGPR1), MHCC-97H-GA (simultaneously expressing GPC3 and ASGPR1) were used.

Effector cell: in vitro cultured CTL cells which were chimeric antigen receptor expressing-positive through FACS detection, as verified in Example 2: GCAR T cell, ACCR T cell, and GZ+28BB T cell.

The effector to target rate was 3:1. The number of target cells was 10000/well, and the number of effector cells corresponded to different effector to target rates. In each group, 5 replicates were set, and the average of the 5 replicate wells was taken. Detection time was 18 h.

Wherein each experiment group and each control group were as follows:

each experiment group: each target cell+T cells expressing different chimeric antigen receptors, Control group 1: maximum release of LDH from target cells, Control group 2: spontaneous release of LDH from target cells, Control group 3: spontaneous release of LDH from effector cells.

Detection method: CytoTox 96 non-radioactive cytotoxicity assay kit (Promega) was used to perform the method. The method is a detection method based on colorimetric method, which can replace 51Cr release method. CytoTox 96® assay quantitatively measures lactate dehydrogenase (LDH). LDH is a stable cytoplasmic enzyme which is released during cell lysis and is released in the same manner as $^{51}$Cr released in radioactivity analysis. The culture supernatant, in which LDH is released, can be detected through enzymatic reaction of 30-minute conjugation, in which LDH converts a tetrazolium salt (INT) into a red formazan. The amount of formed red product is directly proportional to the number of lysed cells. Details can be found in CytoTox 96 non-radioactive cytotoxicity test kit instructions.

The formula for calculating cytotoxicity was:

The experimental results are shown in Table 2. T cells do not exert specific cytotoxic effects on ASGPR1$^-$GPC3$^-$ (MHCC-97H) (MHCC-97H cell, not expressing ASGPR1 or GPC3 gene) and ASGPR1$^+$GPC3$^-$(MHCC-97H-A) (MHCC-97H-A cells, only expressing ASGPR1 instead of GPC3 gene) liver cancer cell, regardless of whether or not the chimeric antigen receptor of the present invention is expressed. However, GCAR T cells and GZ+28BB T cells expressing the chimeric antigen receptors of the present invention are capable of exhibiting a stronger specific cytotoxicity effect on ASGPR1$^-$GPC3$^+$(MHCC-97H-G) cells (MHCC-97H-G cell, only expressing GPC3 instead of ASGPR1 gene) and ASGPR1$^+$GPC3$^+$(MHCC-97H-GA or HepG2) (MHCC-97H-GA or HepG2 cells, expressing ASGPR1 and GPC3 gene) and exhibiting a dependence on effector to target rate gradient, that is, the higher the effector to target rate, the higher the cytotoxicity. The cytotoxicity of GZ+28BB double-infected T cells on MHCC-97H-GA and HepG2 liver cancer cells was 55% and 57% at effector to target rate of 3:1, respectively, and their cytotoxicity was slightly higher than that of GCAR T (35% and 36% respectively).

In contrast, T cells transfected with a virus containing a mock plasmid (empty plasmid vector not carrying GCAR/ACCR) as a blank control did not exert cytotoxic effects on the above five cells.

TABLE 2

|  | Mock T Different effector to target rate | | GCAR T Different effector to target rate | | ACCR T Different effector to target rate | | GZ + 28BB T Different effector to target rate | |
| --- | --- | --- | --- | --- | --- | --- | --- | --- |
| cytotoxicity % | 3:1 | 1:1 | 3:1 | 1:1 | 3:1 | 1:1 | 3:1 | 1:1 |
| MHCC-97H | 1.5 | 1.4 | 1.7 | 1.8 | 1.5 | 1.8 | 1.9 | 2.0 |
| MHCC-97H-A | 1.8 | 1.6 | 2.1 | 2.0 | 2.1 | 1.9 | 2.2 | 1.9 |
| MHCC-97H-G | 1.3 | 1.4 | 31 | 20 | 1.9 | 1.6 | 36 | 25 |
| MHCC-97H-GA | 2.0 | 1.7 | 35 | 23 | 2.0 | 2.1 | 55 | 32 |
| HepG2 | 1.7 | 1.6 | 36 | 25 | 2.1 | 1.8 | 57 | 35 |

Example 5. In Vitro Cell Expansion Experiments

Figure 5:
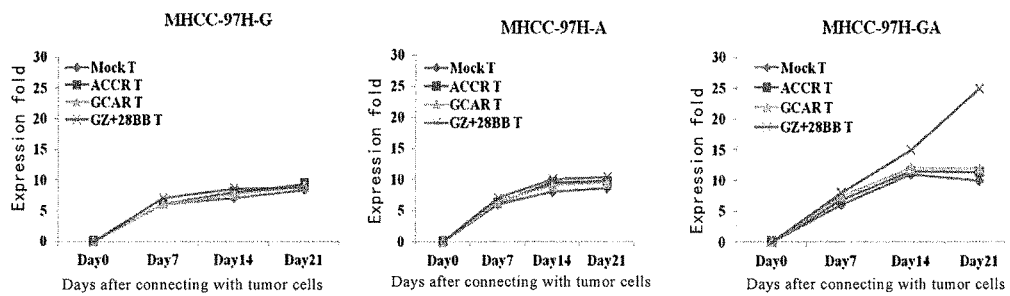
FIG. 5. Detection of proliferation of T cells on day 7, after co-culturing T cells expressing different chimeric antigen receptor and target cells expressing different antigens.

Target cells MHCC-97H-G, MHCC-97H-A, MHCC-97H-GA cells were added into mitomycin (final concentration of 20 μg/mL), incubated at 37° C. for 2 h, washed twice with PBS to remove residual mitomycin. The cells were treated with Trypsin, and suspended into cell suspension. The CTL cells were infected with viruses expressing different chimeric antigen receptors, and then mixed with target cells at a cell density of $5\times10^5$/ml and a ratio of 1:1. The cells were cultured and counted every other day. IL-2 (final concentration of 100 U/ml) was supplemented into passage cell culture, and cells were counted once a week for three weeks in total. Results were as follows: T cells expressing different chimeric antigen receptors were co-cultured with target cells expressing different antigens, and about 6 to 20 times of amplification can be observed on day 7 (see FIG. 5). Compared with other T cells (including GCAR T, ACCR T, Mock T), GZ+28BB T cells have greater amplification ability under the stimulation of double antigens.

Figure 6:
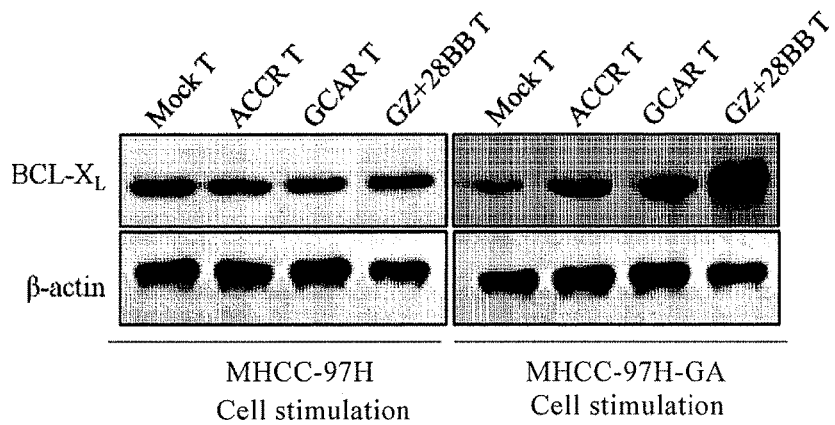
FIG. 6. After co-incubating Mock T, GCAR T, ACCR T and GZ+28BB T lymphocytes with ASGPR1 and GPC3 positively-expressing MHCC-97H-GA cells or ASGPR1 and GPC3 negatively-expressing MHCC-97H cells at an effector to target ratio of 1:1 for 24 h, T lymphocytes were collected and the expression of BCL-XL $X_L$ was detected.

Example 6. ASGPR1/GPC3 Protein Stimulation can Up-Regulate the Expression of BCL-XL in GCAR T, ACCR T and GZ+28BB T Lymphocytes Mock T, GCAR T, ACCR T and GZ+28BB T lymphocytes were incubated with ASGPR1 and GPC3-positively expressed MHCC-97H-GA cells or both negative-expressed MHCC-97H cells at 1:1 for 24 h. T lymphocytes were collected, and the expression of BCL-XL $X_L$ was detected (results shown in FIG. 6). Compared with other transfected T lymphocytes, under stimulation by ASGPR1 and GPC3-positively expressed MHCC-97H-GA cells, the expression level of BCL-$X_L$ in GZ+28BB T cells was up-regulated, indicating that the expression of BCL-$X_L$ in a cell can be up-regulated under the action of CAR and CCR signaling region. The results further suggest that under the stimulation of double antigen (ASGPR1/GPC3), GZ+28BB double-infected T lymphocytes can survive better in the body.

Example 7. In Vivo Antitumor Activity (1) Inoculating tumor: MHCC-97H-A, MHCC-97H-G, MHCC-97H-GA cells were harvested in logarithmic growth phase and $3\times10^6$ cells per mouse were inoculated.

(2) Grouping: In each model of implanted tumor, 6-8 weeks old NOD/SCID mice were randomly divided into 4 groups (n=6). The experimental groups were: No T cell control group, ACCR T treatment group, GCAR T treatment Group, and GZ+28BB T treatment group.

(3) Adoptive transfer of T cells: When the tumor volume in a mouse was about 200 mm$^3$, cyclophosphamide (200 mg/kg) was intraperitoneally injected. The next day, $6\times10^6$/ gene-modified T cells (effector to target ratio of 2:1) or only saline was injected through the tail vein.

(4) The tumor volume was measured and the therapeutic effect of genetically modified T cells on subcutaneous xenografts was observed.

Figure 7:
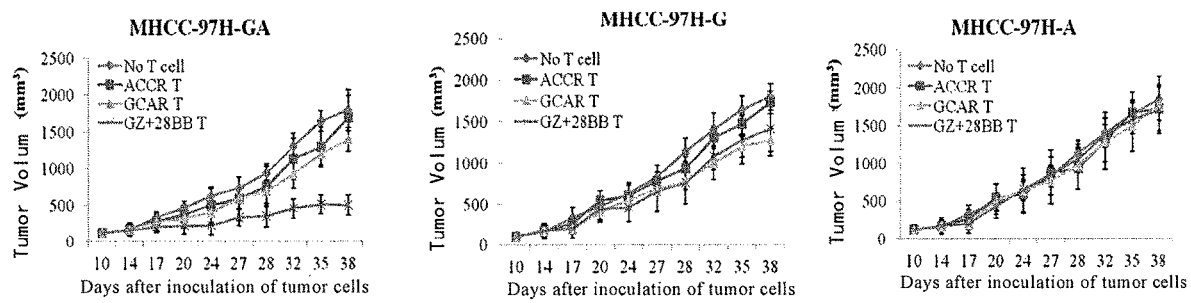
FIG. 7. Detection of in vivo antitumor activity in MHCC-97H-A, MHCC-97H-G, MHCC-97H-GA cells.

Results showed that double-transfected GZ+28BB T genetically modified T lymphocytes significantly inhibited the growth of MHCC-97H-GA cell transplanted tumors expressing double antigens. According to the tumor growth curve shown in FIG. 7, on day 38 after tumor cell inoculation, the size of transplanted tumor of mice in GZ+28BB T cell treatment group was significantly lower than that of other treatment groups (GZ+28BB T vs No T cell, inhibition rate 72%, *$P<0.001$; GZ+28BB T vs ACCR T, inhibition rate 70%, *$P<0.001$; GZ+28BB T vs GCAR T, inhibition rate 64%, ***$P<0.001$). However, both in ASGPR$^+$GPC3$^-$ and ASGPR$^+$GPC3$^-$ transplanted tumor, GZ+28BB T cells did not significantly inhibit tumor growth, indicating that GZ+28BB T cells can significantly inhibit tumor growth only in the presence of double antigens.

Example 8. In Vivo Cell Amplification Experiment

One week after the adoptive transfer of genetically modified T lymphocytes, the number of T cells in peripheral blood was measured.

Figure 8:
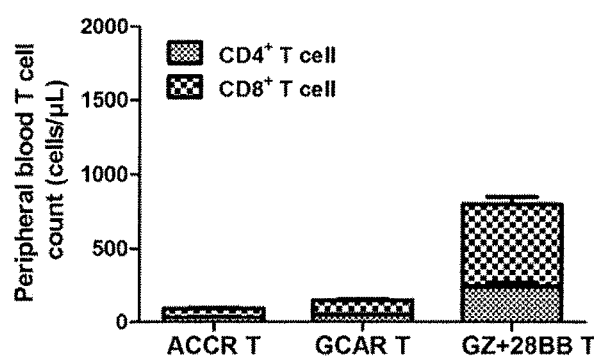
FIG. 8. Detection of the number of T cells in peripheral blood, 1 week after genetically modifying T lymphocytes through adoptive transfer.

(1) ≥50 μL of blood was collected from mouse orbital by using heparin anticoagulant tube;

(2) 20 μL of CD4-FITC/CD8-PE/CD3-PerCP antibody was added into BD TruCount tubes (containing a known number of beads) using an anti-suction pipettes (avoid tip contacting with beads); 50 μL of well-mixed anticoagulant-containing blood was drawn, and the tube cap was covered. The antibody was gently and thoroughly mixed, and incubated at room temperature for 15 min (20-25° C.);

(3) 450 μL of 1×BD FACS lysis buffer was added, the tube cap was covered and the antibody was gently and thoroughly gently mixed, and incubated at room temperature for 15 min (20-25° C.);

(4) To analyze the FACS data, firstly, the PerCP positive cells and the beads were selected. Subsequently, the positive cells were analyzed based on the FITC and PE signals;

(5) the number of two positive cells were calculated;

Number of cells/μL=number of FITC or PE-positive cells×total number of beads/number of beads/50 μL.    Calculation formula:

Results are shown in FIG. 8. In the implanted tumor model inoculating with MHCC-97H-GA cells, the number of T cells in the mouse in GZ+28BB T cells treatment group was significantly higher than that in other treatment groups, suggesting that GZ+28BB T lymphocytes can better survive in the body.

All documents mentioned in the present invention are hereby incorporated by reference as if each individual document was individually incorporated by reference. It is also to be understood that various changes or modifications can be made to the invention by those skilled in the art upon reading the contents of the present invention, and such equivalents fall within the scope of the claims appended hereto.

The invention claimed is:

1. A double-targeted chimeric antigen receptor immune effector cell, wherein the cell expresses the following chimeric receptors:
   a chimeric antigen receptor specifically recognizing Glypican-3 (GPC3); and
   a chimeric antigen receptor specifically recognizing Asialoglycoprotein receptor (ASGPR1); wherein the chimeric antigen receptor specifically recognizing GPC3 comprises: an anti-GPC3 single chain antibody, and one or more T cell stimulatory signaling molecules; and the chimeric costimulatory receptor specifically recognizing ASGPR1 comprises: an anti-ASGPR1 single chain antibody, and a T cell activated co-stimulatory signaling molecule.

2. The chimeric antigen receptor immune effector cell of claim 1, wherein the one or more T cell stimulatory signaling molecules is selected from the group consisting of: CD3ζ and FcεRIγ.

3. The chimeric antigen receptor immune effector cell of claim 1, wherein the T cell activated co-stimulatory signaling molecule is selected from the group consisting of: an intracellular signaling region of a CD27, CD28, CD137, CD134, or ICOS protein, and combinations thereof.

4. The chimeric antigen receptor immune effector cell of claim 1, wherein the immune effector cell is selected from the group consisting of: a T-lymphocyte, a NK cell and a NKT cell.

5. A method for preparing a kit for treating a tumor, wherein the kit comprises: the chimeric antigen receptor immune effector cell of claim 1; and wherein the tumor is a Glypican-3 (GPC3) and Asialoglycoprotein receptor (ASGPR1)-double positive tumor; and preferably the tumor is liver cancer.

6. The chimeric antigen receptor immune effector cell of claim 2, wherein the chimeric antigen receptor specifically recognizing GPC3 comprises: an anti-GPC3 single chain antibody, a transmembrane region of CD8, and CD3ζ.

7. The chimeric antigen receptor immune effector cell of claim 3, wherein the chimeric antigen receptor specifically recognizing ASGPR1 comprises: an anti ASGPR1 single chain antibody, a transmembrane region of CD28, an intracellular signaling region of a CD28 protein, and an intracellular signaling region of a CD137 protein.

8. The chimeric antigen receptor immune effector cell of claim 1, wherein the chimeric antigen receptor specifically recognizing ASGPR1 does not significantly inhibit tumor growth.

9. A double-targeted chimeric antigen receptor immune effector cell, wherein the cell expresses the following chimeric receptors:
   a chimeric antigen receptor specifically recognizing Glypican-3 (GPC3) comprising an anti-GPC3 single chain antibody, a transmembrane region of CD8, and CD3ζ; and
   a chimeric antigen receptor specifically recognizing Asialoglycoprotein receptor (ASGPR1) consisting essentially of an anti ASGPR1 single chain antibody, a transmembrane region of CD28, an intracellular signaling region of a CD28 protein, and an intracellular signaling region of a CD137 protein.

10. The chimeric antigen receptor immune effector cell of claim 9, wherein the chimeric antigen receptor specifically recognizing ASGPR1 does not significantly inhibit tumor growth.

11. The chimeric antigen receptor immune effector cell of claim 9, wherein the chimeric antigen receptor specifically recognizing ASGPR1 does not comprise CD3ζ.

* * * * *

SEQUENCE LISTING

<160> NUMBER OF SEQ ID NOS: 24

<210> SEQ ID NO 1
<211> LENGTH: 54
<212> TYPE: DNA
<213> ORGANISM: Artificial Sequence
<220> FEATURE:
<223> OTHER INFORMATION: synthetic primer

<400> SEQUENCE: 1

| agcttacgcg tcctagcgct accggtcgcc accatggccg ggaccgtgcg cacc | 54 |
|---|---|

<210> SEQ ID NO 2
<211> LENGTH: 38
<212> TYPE: DNA
<213> ORGANISM: Artificial Sequence
<220> FEATURE:
<223> OTHER INFORMATION: synthetic primer

<400> SEQUENCE: 2

| cgaggtcgac ctatcagtgc accaggaaga agaagcac | 38 |
|---|---|

<210> SEQ ID NO 3
<211> LENGTH: 1740
<212> TYPE: DNA
<213> ORGANISM: Homo Sapiens

<400> SEQUENCE: 3

| atggccggga ccgtgcgcac cgcgtgcttg gtggtggcga tgctgctcag cttggacttc | 60 |
|---|---|
| ccgggacagg cgcagccccc gccgccgccg ccggacgcca cctgtcacca gtccgctcc | 120 |
| ttcttccaga gactgcagcc cggactcaag tgggtgccag aaactcccgt gccaggatca | 180 |
| gatttgcaag tatgtctccc taagggccca acatgctgct caagaaagat ggaagaaaaa | 240 |
| taccaactaa cagcacgatt gaacatggaa cagctgcttc agtctgcaag tatggagctc | 300 |
| aagttcttaa ttattcagaa tgctgcggtt ttccaagagg cctttgaaat tgttgttcgc | 360 |
| catgccaaga actacaccaa tgccatgttc aagaacaact acccaagcct gactccacaa | 420 |
| gcttttgagt tgtgggtga attttcaca gatgtgtctc tctacatctt gggttctgac | 480 |
| atcaatgtag atgacatggt caatgaattg tttgacagcc tgtttccagt catctatacc | 540 |
| cagctaatga cccaggcct gcctgattca gccttggaca tcaatgagtg cctccgagga | 600 |
| gcaagacgtg acctgaaagt atttgggaat ttccccaagc ttattatgac ccaggttttcc | 660 |
| aagtcactgc aagtcactag gatcttcctt caggctctga tcttggaat tgaagtgatc | 720 |
| aacacaactg atcacctgaa gttcagtaag gactgtggcc gaatgctcac cagaatgtgg | 780 |
| tactgctctt actgccaggg actgatgatg gttaaaccct gtggcggtta ctgcaatgtg | 840 |
| gtcatgcaag gctgtatggc aggtgtggtg gagattgaca gtactggag agaatacatt | 900 |
| ctgtcccttg aagaacttgt gaatggcatg tacagaatct atgacatgga gaacgtactg | 960 |
| cttggtctct tttcaacaat ccatgattct atccagtatg tccagaagaa tgcaggaaag | 1020 |
| ctgaccacca ctattggcaa gttatgtgcc cattctcaac aacgccaata tagatctgct | 1080 |
| tattatcctg aagatctctt tattgacaag aaagtattaa agttgctca tgtagaacat | 1140 |
| gaagaaacct tatccagccg aagaagggaa ctaattcaga agttgaagtc tttcatcagc | 1200 |
| ttctatagtg ctttgcctgg ctacatctgc agccatagcc tgtggcgga aaacgacacc | 1260 |
| cttttgctgga tggacaaga actcgtggag agatacagcc aaaaggcagc aaggaatgga | 1320 |
| atgaaaaacc agttcaatct ccatgagctg aaaatgaagg ccctgagcc agtggtcagt | 1380 |

```
caaattattg acaaactgaa gcacattaac cagctcctga gaaccatgtc tatgcccaaa    1440
ggtagagttc tggataaaaa cctggatgag gaagggtttg aaagtggaga ctgcggtgat    1500
gatgaagatg agtgcattgg aggctctggt gatggaatga taaaagtgaa gaatcagctc    1560
cgcttccttg cagaactggc ctatgatctg gatgtggatg atgcgcctgg aaacagtcag    1620
caggcaactc cgaaggacaa cgagataagc acctttcaca acctcgggaa cgttcattcc    1680
ccgctgaagc ttctcaccag catggccatc tcggtggtgt gcttcttctt cctggtgcac    1740
```

<210> SEQ ID NO 4
<211> LENGTH: 580
<212> TYPE: PRT
<213> ORGANISM: Homo Sapiens

<400> SEQUENCE: 4

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
                20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
```

```
                305                 310                 315                 320
Leu Gly Leu Phe Ser Thr Ile His Asp Ser Ile Gln Tyr Val Gln Lys
                    325                 330                 335
Asn Ala Gly Lys Leu Thr Thr Thr Ile Gly Lys Leu Cys Ala His Ser
                340                 345                 350
Gln Gln Arg Gln Tyr Arg Ser Ala Tyr Tyr Pro Glu Asp Leu Phe Ile
                355                 360                 365
Asp Lys Lys Val Leu Lys Val Ala His Val Glu His Glu Thr Leu
370                  375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                    405                 410                 415
Glu Asn Asp Thr Leu Cys Trp Asn Gly Gln Leu Val Glu Arg Tyr
                420                 425                 430
Ser Gln Lys Ala Ala Arg Asn Gly Met Lys Asn Gln Phe Asn Leu His
                435                 440                 445
Glu Leu Lys Met Lys Gly Pro Glu Pro Val Val Ser Gln Ile Ile Asp
450                  455                 460
Lys Leu Lys His Ile Asn Gln Leu Leu Arg Thr Met Ser Met Pro Lys
465                 470                 475                 480
Gly Arg Val Leu Asp Lys Asn Leu Asp Glu Glu Gly Phe Glu Ser Gly
                    485                 490                 495
Asp Cys Gly Asp Asp Glu Asp Glu Cys Ile Gly Gly Ser Gly Asp Gly
                500                 505                 510
Met Ile Lys Val Lys Asn Gln Leu Arg Phe Leu Ala Glu Leu Ala Tyr
                515                 520                 525
Asp Leu Asp Val Asp Asp Ala Pro Gly Asn Ser Gln Gln Ala Thr Pro
                530                 535                 540
Lys Asp Asn Glu Ile Ser Thr Phe His Asn Leu Gly Asn Val His Ser
545                 550                 555                 560
Pro Leu Lys Leu Leu Thr Ser Met Ala Ile Ser Val Val Cys Phe Phe
                    565                 570                 575
Phe Leu Val His
            580

<210> SEQ ID NO 5
<211> LENGTH: 54
<212> TYPE: DNA
<213> ORGANISM: Artificial Sequence
<220> FEATURE:
<223> OTHER INFORMATION: synthetic primer

<400> SEQUENCE: 5
gcttacgcgt cctagcgcta ccggtcgcca ccatgaccaa ggagtatcaa gacc        54

<210> SEQ ID NO 6
<211> LENGTH: 37
<212> TYPE: DNA
<213> ORGANISM: Artificial Sequence
<220> FEATURE:
<223> OTHER INFORMATION: synthetic primer

<400> SEQUENCE: 6
cgaggtcgac ctattaaagg agaggtggct cctggct                           37

<210> SEQ ID NO 7
```

<211> LENGTH: 873
<212> TYPE: DNA
<213> ORGANISM: Homo Sapiens

<400> SEQUENCE: 7

```
atgaccaagg agtatcaaga ccttcagcat ctggacaatg aggagagtga ccaccatcag      60
ctcagaaaag ggccacctcc tcccagccc ctcctgcagc gtctctgctc cggacctcgc     120
ctcctcctgc tctccctggg cctcagcctc ctgctgcttg tggttgtctg tgtgatcgga     180
tcccaaaact cccagctgca ggaggagctg cggggcctga gagagacgtt cagcaacttc     240
acagcgagca cggaggccca ggtcaagggc ttgagcaccc aggggaggca agtgggaaga     300
aagatgaagt cgctagagtc ccagctggag aaacagcaga aggacctgag tgaagatcac     360
tccagcctgc tgctccacgt gaagcagttc gtgtctgacc tgcggagcct gagctgtcag     420
atggcggcgc tccagggcaa tggctcagaa aggacctgct gcccggtcaa ctgggtggag     480
cacgagcgca gctgctactg gttctctcgc tccgggaagg cctgggctga cgccgacaac     540
tactgccggc tggaggacgc gcacctggtg gtggtcacgt cctgggagga gcagaaattt     600
gtccagcacc acataggccc tgtgaacacc tggatgggcc tccacgacca aaacgggccc     660
tggaagtggg tggacgggac ggactacgag acgggcttca gaactggag gccggagcag     720
ccggacgact ggtacggcca cgggctcgga ggaggcgagg actgtgccca cttcaccgac     780
gacgccgct ggaacgacga cgtctgccag aggccctacc gctgggtctg cgagacagag     840
ctggacaagg ccagccagga gccacctctc ctt                                  873
```

<210> SEQ ID NO 8
<211> LENGTH: 291
<212> TYPE: PRT
<213> ORGANISM: Homo Sapiens

<400> SEQUENCE: 8

```
Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Ser Leu Gly Leu
        35                  40                  45

Ser Leu Leu Leu Val Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190
```

Thr Ser Trp Glu Glu Gln Lys Phe Val Gln His His Ile Gly Pro Val
        195                 200                 205

Asn Thr Trp Met Gly Leu His Asp Gln Asn Gly Pro Trp Lys Trp Val
        210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Glu Asp Cys Ala
                245                 250                 255

His Phe Thr Asp Asp Gly Arg Trp Asn Asp Val Cys Gln Arg Pro
        260                 265                 270

Tyr Arg Trp Val Cys Glu Thr Glu Leu Asp Lys Ala Ser Gln Glu Pro
        275                 280                 285

Pro Leu Leu
    290

<210> SEQ ID NO 9
<211> LENGTH: 22
<212> TYPE: DNA
<213> ORGANISM: Artificial Sequence
<220> FEATURE:
<223> OTHER INFORMATION: synthetic primer

<400> SEQUENCE: 9
gatgttgtga tgactcagtc tc                                              22

<210> SEQ ID NO 10
<211> LENGTH: 34
<212> TYPE: DNA
<213> ORGANISM: Artificial Sequence
<220> FEATURE:
<223> OTHER INFORMATION: synthetic primer

<400> SEQUENCE: 10
gcgctggcgt cgtggttgag gagacggtga ccag                                 34

<210> SEQ ID NO 11
<211> LENGTH: 729
<212> TYPE: DNA
<213> ORGANISM: Artificial Sequence
<220> FEATURE:
<223> OTHER INFORMATION: synthetic scFv (GPC3) polynucleotide sequence

<400> SEQUENCE: 11
gatgttgtga tgactcagtc tccactctcc ctgcccgtca cccctggaga gccggcctcc      60
atctcctgca gatctagtca gagccttgta cacagtaatg ccaacaccta tttacattgg    120
tacctgcaga agccagggca gtctccacag ctcctgatct ataaagtttc caaccgattt    180
tctggggtcc ctgacaggtt cagtggcagt ggatcaggca cagattttac actgaaaatc    240
agcagagtgg aggctgagga tgttggggtt tattactgct ctcaaaatac acatgttcct    300
cctacgtttg gccaggggac caagctggag atcaaacgtg gtggaggcgg ttcaggcgga    360
ggtggctctg gcggtggcgg atcgcaggtg cagctggtgc agtctggagc tgaggtgaag    420
aagcctgggg cctcagtgaa ggtctcctgc aaggcttctg gatacacctt caccgactat    480
gaaatgcact gggtgcgaca ggcccctgga caagggcttg agtggatggg agctcttgat    540
cctaaaactg gtgatactgc ctacagtcag aagttcaagg gcagagtcac gctgaccgcg    600
gacgaatcca cgagcacagc ctacatggag ctgagcagcc tgagatctga ggacacggcc    660
gtgtattact gtacaagatt ctactcctat acttactggg gccagggaac cctggtcacc    720
gtctcctca                                                                    729

<210> SEQ ID NO 12
<211> LENGTH: 243
<212> TYPE: PRT
<213> ORGANISM: Artificial Sequence
<220> FEATURE:
<223> OTHER INFORMATION: synthetic scFv (GPC3) polypeptide sequence

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Asp Tyr
145                 150                 155                 160

Glu Met His Trp Val Arg Gln Ala Pro Gly Gln Gly Leu Glu Trp Met
                165                 170                 175

Gly Ala Leu Asp Pro Lys Thr Gly Asp Thr Ala Tyr Ser Gln Lys Phe
            180                 185                 190

Lys Gly Arg Val Thr Leu Thr Ala Asp Glu Ser Thr Ser Thr Ala Tyr
        195                 200                 205

Met Glu Leu Ser Ser Leu Arg Ser Glu Asp Thr Ala Val Tyr Tyr Cys
    210                 215                 220

Thr Arg Phe Tyr Ser Tyr Thr Tyr Trp Gly Gln Gly Thr Leu Val Thr
225                 230                 235                 240

Val Ser Ser

<210> SEQ ID NO 13
<211> LENGTH: 25
<212> TYPE: DNA
<213> ORGANISM: Artificial Sequence
<220> FEATURE:
<223> OTHER INFORMATION: synthetic primer

<400> SEQUENCE: 13
accacgacgc cagcgccgcg accac                                                   25

<210> SEQ ID NO 14
<211> LENGTH: 39
<212> TYPE: DNA
<213> ORGANISM: Artificial Sequence
<220> FEATURE:
<223> OTHER INFORMATION: synthetic primer

```
<400> SEQUENCE: 14
gaggtcgacc tagcgagggg gcagggcctg catgtgaag                             39

<210> SEQ ID NO 15
<211> LENGTH: 52
<212> TYPE: DNA
<213> ORGANISM: Artificial Sequence
<220> FEATURE:
<223> OTHER INFORMATION: synthetic primer

<400> SEQUENCE: 15
cttacgcgtc ctagcgctac cggtcgccac catggtgagc aagggcgagg ag             52

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
cggcctggcg gcgtggagca g                                                21

<210> SEQ ID NO 17
<211> LENGTH: 2118
<212> TYPE: DNA
<213> ORGANISM: Artificial Sequence
<220> FEATURE:
<223> OTHER INFORMATION: synthetic eGFP-F2A-GPC3-CD3-zeta polynucleotide
      sequence
<220> FEATURE:
<221> NAME/KEY: misc_feature
<223> OTHER INFORMATION: polynucleotide

<400> SEQUENCE: 17
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtcc     720
ggagtgaaac agactttgaa ttttgacctt ctgaagttgg caggagacgt tgagtccaac     780
cctgggccca tggccttacc agtgaccgcc ttgctcctgc cgctggcctt gctgctccac     840
gccgccaggc cggatgttgt gatgactcag tctccactct ccctgcccgt cacccctgga     900
gagccggcct ccatctcctg cagatctagt cagagccttg tacacagtaa tgccaacacc     960
tatttacatt ggtacctgca gaagccaggg cagtctccac agctcctgat ctataaagtt    1020
tccaaccgat tttctggggt ccctgacagg ttcagtggca gtggatcagg cacagatttt    1080
```

```
acactgaaaa tcagcagagt ggaggctgag gatgttgggg tttattactg ctctcaaaat    1140
acacatgttc ctcctacgtt tggccagggg accaagctgg agatcaaacg tggtggaggc    1200
ggttcaggcg gaggtggctc tggcggtggc ggatcgcagg tgcagctggt gcagtctgga    1260
gctgaggtga agaagcctgg ggcctcagtg aaggtctcct gcaaggcttc tggatacacc    1320
ttcaccgact atgaaatgca ctgggtgcga caggcccctg acaagggct tgagtggatg     1380 ggagctcttg atcctaaaac tggtgatact gcctacagtc agaagttcaa gggcagagtc    1440
acgctgaccg cggacgaatc cacgagcaca gcctacatgg agctgagcag cctgagatct    1500
gaggacacgg ccgtgtatta ctgtacaaga ttctactcct atacttactg gggccaggga    1560
accctggtca ccgtctcctc aaccacgacg ccagcgccgc gaccaccaac accggcgccc    1620
accatcgcgt cgcagcccct gtccctgcgc ccagaggcgt gccggccagc ggcggggggc    1680
gcagtgcaca cgagggggct ggacttcgcc tgtgatatct acatctgggc gcccttggcc    1740
gggacttgtg gggtccttct cctgtcactg gttatcacca gagtgaagtt cagcaggagc    1800
gcagacgccc ccgcgtacca gcaggccag aaccagctct ataacgagct caatctagga    1860
cgaagagagg agtacgatgt tttggacaag agacgtggcc gggaccctga tgggggga     1920 aagccgcaga gaaggaagaa ccctcaggaa ggcctgtaca atgaactgca gaaagataag    1980
atggcggagg cctacagtga gattgggatg aaaggcgagc gccggagggg caaggggcac    2040
gatggccttt accagggtct cagtacagcc accaaggaca cctacgacgc ccttcacatg    2100
caggccctgc cccctcgc                                                   2118
```

<210> SEQ ID NO 18
<211> LENGTH: 706
<212> TYPE: PRT
<213> ORGANISM: Artificial Sequence
<220> FEATURE:
<223> OTHER INFORMATION: synthetic eGFP-F2A-GPC3-CD3-zeta polypeptide
      sequence
<220> FEATURE:
<221> NAME/KEY: MISC_FEATURE
<223> OTHER INFORMATION: polypeptide

<400> SEQUENCE: 18

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Val Lys Gln Thr Leu Asn Phe Asp Leu Leu Lys Leu Ala Gly Asp
                245                 250                 255

Val Glu Ser Asn Pro Gly Pro Met Ala Leu Pro Val Thr Ala Leu Leu
            260                 265                 270

Leu Pro Leu Ala Leu Leu Leu His Ala Ala Arg Pro Asp Val Val Met
        275                 280                 285

Thr Gln Ser Pro Leu Ser Leu Pro Val Thr Pro Gly Glu Pro Ala Ser
    290                 295                 300

Ile Ser Cys Arg Ser Ser Gln Ser Leu Val His Ser Asn Ala Asn Thr
305                 310                 315                 320

Tyr Leu His Trp Tyr Leu Gln Lys Pro Gly Gln Ser Pro Gln Leu Leu
                325                 330                 335

Ile Tyr Lys Val Ser Asn Arg Phe Ser Gly Val Pro Asp Arg Phe Ser
            340                 345                 350

Gly Ser Gly Ser Gly Thr Asp Phe Thr Leu Lys Ile Ser Arg Val Glu
        355                 360                 365

Ala Glu Asp Val Gly Val Tyr Tyr Cys Ser Gln Asn Thr His Val Pro
    370                 375                 380

Pro Thr Phe Gly Gln Gly Thr Lys Leu Glu Ile Lys Arg Gly Gly Gly
385                 390                 395                 400

Gly Ser Gly Gly Gly Gly Ser Gly Gly Gly Gly Ser Gln Val Gln Leu
                405                 410                 415

Val Gln Ser Gly Ala Glu Val Lys Lys Pro Gly Ala Ser Val Lys Val
            420                 425                 430

Ser Cys Lys Ala Ser Gly Tyr Thr Phe Thr Asp Tyr Glu Met His Trp
        435                 440                 445

Val Arg Gln Ala Pro Gly Gln Gly Leu Glu Trp Met Gly Ala Leu Asp
    450                 455                 460

Pro Lys Thr Gly Asp Thr Ala Tyr Ser Gln Lys Phe Lys Gly Arg Val
465                 470                 475                 480

Thr Leu Thr Ala Asp Glu Ser Thr Ser Thr Ala Tyr Met Glu Leu Ser
                485                 490                 495

Ser Leu Arg Ser Glu Asp Thr Ala Val Tyr Tyr Cys Thr Arg Phe Tyr
            500                 505                 510

Ser Tyr Thr Tyr Trp Gly Gln Gly Thr Leu Val Thr Val Ser Ser Thr
        515                 520                 525

Thr Thr Pro Ala Pro Arg Pro Pro Thr Pro Ala Pro Thr Ile Ala Ser
    530                 535                 540

Gln Pro Leu Ser Leu Arg Pro Glu Ala Cys Arg Pro Ala Ala Gly Gly
545                 550                 555                 560

Ala Val His Thr Arg Gly Leu Asp Phe Ala Cys Asp Ile Tyr Ile Trp
                565                 570                 575
```

```
Ala Pro Leu Ala Gly Thr Cys Gly Val Leu Leu Ser Leu Val Ile
            580                 585                 590

Thr Arg Val Lys Phe Ser Arg Ser Ala Asp Ala Pro Ala Tyr Gln Gln
        595                 600                 605

Gly Gln Asn Gln Leu Tyr Asn Glu Leu Asn Leu Gly Arg Arg Glu Glu
    610                 615                 620

Tyr Asp Val Leu Asp Lys Arg Gly Arg Asp Pro Glu Met Gly Gly
625                 630                 635                 640

Lys Pro Gln Arg Arg Lys Asn Pro Gln Glu Gly Leu Tyr Asn Glu Leu
                645                 650                 655

Gln Lys Asp Lys Met Ala Glu Ala Tyr Ser Glu Ile Gly Met Lys Gly
            660                 665                 670

Glu Arg Arg Arg Gly Lys Gly His Asp Gly Leu Tyr Gln Gly Leu Ser
        675                 680                 685

Thr Ala Thr Lys Asp Thr Tyr Asp Ala Leu His Met Gln Ala Leu Pro
    690                 695                 700

Pro Arg
705

<210> SEQ ID NO 19
<211> LENGTH: 360
<212> TYPE: DNA
<213> ORGANISM: Artificial Sequence
<220> FEATURE:
<223> OTHER INFORMATION: synthetic polynucleotide sequence - anti-ASGPR
      single domain antibody

<400> SEQUENCE: 19
gaggtgcagc tgttggagtc tgggggaggc ttggtacagc ctggggggtc cctgcgtctc      60
tcctgtgcag cctccggatt cacctttgag aagtatgcga tggcgtgggt ccgccaggcc     120
ccagggaagg gtctggagtg gtctcacgg atttcggcga ggggtgtgac gacatactac      180
gcagactccg tgaagggccg gttcaccatc tcccgcgaca attccaagaa cacgctgtat     240
ctgcaaatga acagcctgcg tgctgaggac accgcggtat attactgtgc gaaacataag     300
cggcacgagc atactcgttt tgactcctgg ggtcagggaa ccctggtcac cgtctcgagc     360

<210> SEQ ID NO 20
<211> LENGTH: 120
<212> TYPE: PRT
<213> ORGANISM: Artificial Sequence
<220> FEATURE:
<223> OTHER INFORMATION: synthetic polypeptide sequence - anti-ASGPR
      single domain antibody

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Lys Tyr
            20                  25                  30

Ala Met Ala Trp Val Arg Gln Ala Pro Gly Lys Gly Leu Glu Trp Val
        35                  40                  45

Ser Arg Ile Ser Ala Arg Gly Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys His Lys Arg His Glu His Thr Arg Phe Asp Ser Trp Gly Gln
            100                 105                 110

Gly Thr Leu Val Thr Val Ser Ser
        115                 120

<210> SEQ ID NO 21
<211> LENGTH: 31
<212> TYPE: DNA
<213> ORGANISM: Artificial Sequence
<220> FEATURE:
<223> OTHER INFORMATION: synthetic primer

<400> SEQUENCE: 21
gaggtcgacc tacagttcac atcctccttc t                           31

<210> SEQ ID NO 22
<211> LENGTH: 28
<212> TYPE: DNA
<213> ORGANISM: Artificial Sequence
<220> FEATURE:
<223> OTHER INFORMATION: synthetic primer

<400> SEQUENCE: 22
gaggtcgacc tacagttcac atcctcct                               28

<210> SEQ ID NO 23
<211> LENGTH: 1668
<212> TYPE: DNA
<213> ORGANISM: Artificial Sequence
<220> FEATURE:
<223> OTHER INFORMATION: synthetic polynucleotide - mCherry-F2A-ASGPR-
      CD28a-CD28b-CD137

<400> SEQUENCE: 23
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttccccg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact cccctccgga cggcccgta   420 atgcagaaga gaccatgggg ctgggaggcc tcctccgagc ggatgtaccc cgaggacggc   480
gccctgaagg gcgagatcaa gcagaggctg aagctgaagg acggcggcca ctacgacgct   540
gaggtcaaga ccacctacaa ggccaagaag cccgtgcagc tgcccggcgc ctacaacgtc   600
aacatcaagt tggacatcac ctcccacaac gaggactaca ccatcgtgga acagtacgaa   660
cgcgccgagg ccgccactc caccggcggc atggacgagc tgtacaagtc cggagtgaaa   720
cagactttga attttgacct tctgaagttg caggagacg ttgagtccaa ccctgggccc   780
atggccttac cagtgaccgc cttgctcctg ccgctggcct tgctgctcca cgccgccagg   840
ccggaggtgc agctgttgga gtctgggga ggcttggtac agcctggggg gtccctgcgt   900
ctctcctgtg cagcctccgg attcaccttt gagaagtatg cgatgcgtg gtccgccag   960 gccccaggga agggtctgga gtgggtctca cggatttcgg cgagggtgt gacgacatac  1020 tacgcagact ccgtgaaggg ccggttcacc atctcccgcg acaattccaa gaacacgctg  1080
tatctgcaaa tgaacagcct gcgtgctgag gacaccgcgg tatattactg tgcgaaacat  1140

```
aagcggcacg agcatactcg ttttgactcc tggggtcagg gaaccctggt caccgtctcg    1200
agcaccacga cgccagcgcc gcgaccacca acaccggcgc ccaccatcgc gtcgcagccc    1260
ctgtccctgc gcccagaggc gtgccggcca gcggcggggg gcgcagtgca cacgaggggg    1320
ctggacttcg cctgtgattt ttgggtgctg gtggtggttg gtggagtcct ggcttgctat    1380
agcttgctag taacagtggc ctttattatt ttctgggtga ggagtaagag gagcaggctc    1440
ctgcacagtg actacatgaa catgactccc gccgccccg ggccaacccg caagcattac    1500
cagccctatg ccccaccacg cgacttcgca gcctatcgct ccaaacgggg cagaaagaaa    1560
ctcctgtata tattcaaaca accatttatg agaccagtac aaactactca agaggaagat    1620
ggctgtagct gccgatttcc agaagaagaa gaaggaggat gtgaactg                 1668
```

<210> SEQ ID NO 24
<211> LENGTH: 556
<212> TYPE: PRT
<213> ORGANISM: Artificial Sequence
<220> FEATURE:
<223> OTHER INFORMATION: synthetic polypeptide - mCherry-F2A-ASGPR-CD28a-CD28b-CD137

<400> SEQUENCE: 24

```
Met Val Ser Lys Gly Glu Glu Asp Asn Met Ala Ile Ile Lys Glu Phe
  1               5                  10                  15

Met Arg Phe Lys Val His Met Glu Gly Ser Val Asn Gly His Glu Phe
             20                  25                  30

Glu Ile Glu Gly Glu Gly Glu Gly Arg Pro Tyr Glu Gly Thr Gln Thr
         35                  40                  45

Ala Lys Leu Lys Val Thr Lys Gly Gly Pro Leu Pro Phe Ala Trp Asp
     50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Val Lys
225                 230                 235                 240

Gln Thr Leu Asn Phe Asp Leu Leu Lys Leu Ala Gly Asp Val Glu Ser
                245                 250                 255

Asn Pro Gly Pro Met Ala Leu Pro Val Thr Ala Leu Leu Leu Pro Leu
            260                 265                 270
```

```
Ala Leu Leu Leu His Ala Ala Arg Pro Glu Val Gln Leu Leu Glu Ser
        275                 280                 285

Gly Gly Gly Leu Val Gln Pro Gly Gly Ser Leu Arg Leu Ser Cys Ala
        290                 295                 300

Ala Ser Gly Phe Thr Phe Glu Lys Tyr Ala Met Ala Trp Val Arg Gln
305                 310                 315                 320

Ala Pro Gly Lys Gly Leu Glu Trp Val Ser Arg Ile Ser Ala Arg Gly
                325                 330                 335

Val Thr Thr Tyr Tyr Ala Asp Ser Val Lys Gly Arg Phe Thr Ile Ser
                340                 345                 350

Arg Asp Asn Ser Lys Asn Thr Leu Tyr Leu Gln Met Asn Ser Leu Arg
        355                 360                 365

Ala Glu Asp Thr Ala Val Tyr Tyr Cys Ala Lys His Lys Arg His Glu
        370                 375                 380

His Thr Arg Phe Asp Ser Trp Gly Gln Gly Thr Leu Val Thr Val Ser
385                 390                 395                 400

Ser Thr Thr Thr Pro Ala Pro Arg Pro Pro Thr Pro Ala Pro Thr Ile
                405                 410                 415

Ala Ser Gln Pro Leu Ser Leu Arg Pro Glu Ala Cys Arg Pro Ala Ala
                420                 425                 430

Gly Gly Ala Val His Thr Arg Gly Leu Asp Phe Ala Cys Asp Phe Trp
        435                 440                 445

Val Leu Val Val Val Gly Gly Val Leu Ala Cys Tyr Ser Leu Leu Val
        450                 455                 460

Thr Val Ala Phe Ile Ile Phe Trp Val Arg Ser Lys Arg Ser Arg Leu
465                 470                 475                 480

Leu His Ser Asp Tyr Met Asn Met Thr Pro Arg Arg Pro Gly Pro Thr
                485                 490                 495

Arg Lys His Tyr Gln Pro Tyr Ala Pro Pro Arg Asp Phe Ala Ala Tyr
                500                 505                 510

Arg Ser Lys Arg Gly Arg Lys Lys Leu Leu Tyr Ile Phe Lys Gln Pro
        515                 520                 525

Phe Met Arg Pro Val Gln Thr Thr Gln Glu Glu Asp Gly Cys Ser Cys
        530                 535                 540

Arg Phe Pro Glu Glu Glu Glu Gly Gly Cys Glu Leu
545                 550                 555
```